US009872609B2

(12) United States Patent
Levy

(10) Patent No.: US 9,872,609 B2
(45) **Date of Patent: *Jan. 23, 2018**

(54) MULTI-CAMERA ENDOSCOPE

(71) Applicant: EndoChoice Innovation Center Ltd., Caesarea (IL)

(72) Inventor: Avi Levy, Herzliya (IL)

(73) Assignee: EndoChoice Innovation Center Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,120

(22) Filed: Oct. 18, 2012

(65) Prior Publication Data

US 2013/0109916 A1 May 2, 2013

Related U.S. Application Data

(63) Continuation-in-part of application No. 13/119,032, filed as application No. PCT/IL2010/000476 on Jun. 16, 2010, now Pat. No. 9,554,692.

(Continued)

(51) Int. Cl.
*A61B 1/05* (2006.01)
*A61B 1/06* (2006.01)
(Continued)

(52) U.S. Cl.
CPC .......... *A61B 1/042* (2013.01); *A61B 1/00096* (2013.01); *A61B 1/00174* (2013.01);
(Continued)

(58) Field of Classification Search
CPC ....... A61B 1/0052; A61B 1/018; A61B 1/042; A61B 1/015; A61B 1/05; A61B 1/00096;
(Continued)

(56) References Cited

U.S. PATENT DOCUMENTS

| | | | |
|---|---|---|---|
| 4,084,401 | A | 4/1978 | Belardi |
| 4,253,448 | A | 3/1981 | Terada |

(Continued)

FOREIGN PATENT DOCUMENTS

| | | |
|---|---|---|
| CN | 1376443 | 10/2002 |
| CN | 2829646 Y | 10/2006 |

(Continued)

OTHER PUBLICATIONS

JP 2006-68109 A, "Spherical Capsule Type Omnidirectional Endoscope" inventor: Fujimoto et al. , Nagoya Institute of Technology, Date of filing: Aug. 31, 2004.*

(Continued)

*Primary Examiner* — John P Leubecker
*Assistant Examiner* — Rajaa El Alami
(74) *Attorney, Agent, or Firm* — Bookoff McAndrews, PLLC

(57) ABSTRACT

There is provided herein a tip section of a multi-camera endoscope, the tip section comprising a front-pointing camera and a discrete front illuminator associated therewith two or more side-pointing cameras positioned at or in proximity to a distal end of said tip section, wherein each of said two or more side-pointing cameras having a discrete side illuminator associated therewith, and a working channel configured for insertion of a surgical tool.

18 Claims, 8 Drawing Sheets

Related U.S. Application Data

(60) Provisional application No. 61/218,085, filed on Jun. 18, 2009.

(51) Int. Cl.
*A61B 1/015* (2006.01)
*A61B 1/04* (2006.01)
*A61B 1/00* (2006.01)

(52) U.S. Cl.
CPC ...... *A61B 1/00177* (2013.01); *A61B 1/00181* (2013.01); *A61B 1/0684* (2013.01)

(58) Field of Classification Search
CPC ............ A61B 1/00174; A61B 1/00177; A61B 1/00181; A61B 1/0684
USPC ................ 600/156–160, 163, 173, 176–178, 600/180–182
See application file for complete search history.

(56) References Cited

U.S. PATENT DOCUMENTS 4,261,345 A 4/1981 Yamaguchi
4,402,313 A 9/1983 Yabe
4,414,608 A 11/1983 Furihata
4,439,030 A 3/1984 Ueda
4,469,090 A 9/1984 Konomura
4,494,549 A 1/1985 Namba
4,522,196 A 6/1985 Cunningham et al.
4,565,423 A 1/1986 Ueda
4,576,144 A 3/1986 Ishii
4,588,294 A 5/1986 Siegmund
4,590,923 A 5/1986 Watanabe
4,641,635 A 2/1987 Yabe
4,699,463 A 10/1987 D
4,708,126 A 11/1987 Toda
4,727,859 A 3/1988 Lia
4,736,732 A 4/1988 Shimonaka
4,753,222 A 6/1988 Morishita
4,764,001 A 8/1988 Yokota
4,794,913 A 1/1989 Shimonaka
4,801,792 A 1/1989 Yamasita
4,841,952 A 6/1989 Sato
4,846,154 A 7/1989 MacAnally et al.
4,868,644 A 9/1989 Yabe
4,877,314 A 10/1989 Kanamori
4,878,485 A 11/1989 Adair
4,888,639 A 12/1989 Yabe
4,902,115 A 2/1990 Takahashi
4,905,670 A 3/1990 Adair
4,914,521 A 4/1990 Adair
4,974,075 A 11/1990 Nakajima
4,976,522 A 12/1990 Igarashi
4,982,724 A 1/1991 Saito
4,984,878 A 1/1991 Miyano
4,998,182 A 3/1991 Krauter
5,166,787 A 11/1992 Irion
5,193,525 A 3/1993 Silverstein
5,239,983 A 8/1993 Katsurada
5,296,971 A 3/1994 Mori
5,299,561 A 4/1994 Yoshimoto
5,305,121 A 4/1994 Moll
5,309,227 A 5/1994 Inoue
5,313,934 A 5/1994 Wiita et al.
5,339,800 A 8/1994 Wiita et al.
5,359,456 A 10/1994 Kikuchi
5,380,049 A 1/1995 Smowton
5,398,056 A 3/1995 Yabe
5,408,623 A 4/1995 Dolidon
5,412,478 A 5/1995 Ishihara
5,420,644 A 5/1995 Watanabe
5,432,543 A 7/1995 Hasegawa
5,436,767 A 7/1995 Suzuki
5,447,148 A 9/1995 Oneda
5,452,391 A 9/1995 Chou
5,460,167 A 10/1995 Yabe
5,483,951 A 1/1996 Frassica
5,485,316 A 1/1996 Mori
5,489,256 A 2/1996 Adair
5,507,717 A 4/1996 Kura
5,512,940 A 4/1996 Takasugi
5,515,449 A 5/1996 Tsuruoka
5,518,501 A 5/1996 Oneda
5,518,502 A 5/1996 Kaplan
5,547,455 A * 8/1996 McKenna ............ A61B 1/0005 348/65
5,547,457 A 8/1996 Tsuyuki
5,550,582 A 8/1996 Takasugi
5,585,840 A 12/1996 Watanabe
5,587,839 A 12/1996 Miyano
5,589,874 A 12/1996 Buchin
5,592,216 A 1/1997 Uehara
5,605,530 A 2/1997 Fischell
5,609,560 A 3/1997 Ichikawa
5,617,136 A 4/1997 Iso
5,630,782 A 5/1997 Adair
5,653,677 A 8/1997 Okada
5,656,011 A 8/1997 Uihlein
5,662,588 A 9/1997 Iida
5,675,378 A 10/1997 Takasugi
5,679,110 A 10/1997 Hamazaki
5,685,823 A * 11/1997 Ito ...................... A61B 1/00091 600/121
5,701,155 A 12/1997 Wood
5,702,345 A 12/1997 Wood
5,702,347 A 12/1997 Yabe
5,707,344 A 1/1998 Nakazawa
5,716,323 A 2/1998 Lee
5,725,474 A 3/1998 Yasui
5,725,476 A 3/1998 Yasui
5,725,477 A 3/1998 Yasui
5,728,045 A 3/1998 Komi
5,751,340 A 5/1998 Strobl
5,764,809 A 6/1998 Nomami
5,777,797 A 7/1998 Miyano
5,782,751 A 7/1998 Matsuno
5,793,539 A 8/1998 Konno
5,800,341 A 9/1998 McKenna et al.
5,812,187 A 9/1998 Watanabe
5,830,124 A 11/1998 Suzuki
5,836,894 A 11/1998 Sarvazyan
5,852,511 A 12/1998 Tateyama
5,860,913 A 1/1999 Yamaya
5,870,234 A 2/1999 EbbesmeierneeSchitthof
5,871,439 A 2/1999 Takahashi
5,871,440 A 2/1999 Okada
5,876,326 A 3/1999 Takamura
5,879,284 A 3/1999 Tsujita
5,894,322 A 4/1999 Hamano
5,912,764 A 6/1999 Togino
5,913,817 A 6/1999 Lee
5,914,810 A 6/1999 Watts
5,916,148 A 6/1999 Tsuyuki
5,929,901 A 7/1999 Adair
5,930,424 A 7/1999 Heimberger
5,933,275 A 8/1999 Igarashi
5,933,282 A 8/1999 Tomioka
5,936,773 A 8/1999 Togino
5,940,126 A * 8/1999 Kimura ................ H04N 3/1593 348/218.1
5,961,445 A 10/1999 Chikama
5,969,888 A 10/1999 Sukekawa
5,986,693 A 11/1999 Adair
5,989,185 A 11/1999 Miyazaki
5,993,037 A 11/1999 Tomioka
5,995,136 A 11/1999 Hattori
6,009,189 A 12/1999 Schaack
6,025,873 A 2/2000 Nishioka
6,043,839 A 3/2000 Adair
6,069,698 A 5/2000 Ozawa
6,080,104 A 6/2000 Ozawa
6,104,540 A 8/2000 Hayakawa
6,110,127 A 8/2000 Suzuki

(56) References Cited

U.S. PATENT DOCUMENTS 6,117,068 A 9/2000 Gourley
6,124,989 A 9/2000 Oode
6,139,175 A 10/2000 Tomioka
6,139,490 A 10/2000 Breidenthal et al.
6,147,808 A 11/2000 Togino
6,163,401 A 12/2000 Igarashi
6,166,858 A 12/2000 Togino
6,181,481 B1 1/2001 Yamamoto
6,184,923 B1 2/2001 Miyazaki
6,185,046 B1 2/2001 Togino
6,196,967 B1 3/2001 Lim
6,201,646 B1 3/2001 Togino
6,201,648 B1 3/2001 Togino
6,210,322 B1 4/2001 Byrne
6,211,904 B1 4/2001 Adair
6,215,517 B1 4/2001 Takahashi
6,217,500 B1 4/2001 Helseth
6,245,086 B1 6/2001 Storz
6,249,391 B1 6/2001 Hayakawa
6,260,994 B1 7/2001 Matsumoto
6,261,226 B1 7/2001 McKenna
6,275,255 B1 8/2001 Adair
6,295,368 B1 9/2001 Hasegawa
6,306,082 B1 10/2001 Takahashi et al.
6,310,642 B1 10/2001 Adair
6,310,736 B1 10/2001 Togino
6,315,712 B1 11/2001 Rovegno
6,322,496 B1 11/2001 Iida
6,327,094 B1 12/2001 Aoki
6,327,101 B1 12/2001 Miyano
6,334,845 B1 1/2002 Higuchi
6,353,504 B1 3/2002 Yamamoto
6,375,610 B2 4/2002 Verschuur
6,387,045 B1 5/2002 Takahashi
6,398,723 B1 6/2002 Kehr
6,400,514 B2 6/2002 Minami
6,422,995 B2 7/2002 Akiba
6,425,857 B1 7/2002 Rudischhauser
6,450,950 B2 9/2002 Irion
6,461,304 B1 10/2002 Tanaka
6,464,631 B1 10/2002 Girke et al.
6,464,633 B1 10/2002 Hosoda
6,468,201 B1 10/2002 Burdick
6,468,202 B1 10/2002 Irion
6,471,636 B1 10/2002 Sano
6,471,637 B1 10/2002 Green
6,473,116 B1 10/2002 Takahashi
6,476,851 B1 11/2002 Nakamura
6,500,115 B2 12/2002 Krattiger
6,514,210 B2 2/2003 Ohara
6,520,908 B1 2/2003 Ikeda
6,527,704 B1 3/2003 Chang et al.
6,530,881 B1 3/2003 Ailinger
6,533,722 B2 3/2003 Nakashima
6,545,703 B1 4/2003 Takahashi
6,551,239 B2 4/2003 Renner
6,554,767 B2 4/2003 Tanaka
6,567,114 B2 5/2003 Takahashi
6,569,084 B1 5/2003 Mizuno
6,582,361 B2 6/2003 Hirano
6,589,168 B2 7/2003 Thompson
6,606,113 B2 8/2003 Nakamura
6,618,205 B2 9/2003 Murayama
D481,125 S 10/2003 Hayamizu
6,638,212 B1 10/2003 Oshima
6,638,214 B2 * 10/2003 Akiba .......................... 600/157
6,641,531 B2 11/2003 Kehr
6,656,111 B2 12/2003 Fujii
6,671,099 B2 12/2003 Nagata
6,677,983 B1 1/2004 Takahashi
6,677,984 B2 1/2004 Kobayashi
6,677,992 B1 1/2004 Matsumoto
6,692,430 B2 2/2004 Adler
6,692,431 B2 2/2004 Kazakevich
6,699,181 B2 3/2004 Wako
6,699,185 B2 3/2004 Gminder
6,704,052 B1 3/2004 Togino
6,712,760 B2 3/2004 Sano
D490,898 S 6/2004 Hayamizu
6,764,439 B2 7/2004 Schaaf
6,778,208 B2 8/2004 Takeshige
6,788,343 B1 9/2004 Togino
6,793,621 B2 9/2004 Butler
6,801,325 B2 10/2004 Farr
6,809,499 B2 10/2004 Solingen
6,809,866 B2 10/2004 Xie
6,829,003 B2 12/2004 Takami
6,832,984 B2 12/2004 Stelzer
6,844,985 B2 1/2005 Murayama
6,846,311 B2 1/2005 Gatto
6,849,043 B2 2/2005 Kondo
6,860,516 B2 3/2005 Ouchi
6,876,380 B2 4/2005 Abe
6,887,194 B2 5/2005 Hart
6,888,119 B2 5/2005 Iizuka
6,898,086 B2 5/2005 Takami
6,899,673 B2 5/2005 Ogura
6,900,829 B1 5/2005 Ozawa
6,900,950 B2 5/2005 Nagata
6,902,529 B2 6/2005 Onishi
6,903,761 B1 6/2005 Abe
6,918,693 B2 7/2005 Ota
6,921,362 B2 7/2005 Ouchi
6,930,705 B2 8/2005 Tanaka
6,933,962 B2 8/2005 Yamamoto
6,937,267 B1 8/2005 Takahashi
6,937,269 B2 8/2005 Sugimoto
6,943,821 B2 9/2005 Abe
6,943,822 B2 9/2005 Iida
6,944,031 B2 9/2005 Takami
6,945,929 B2 9/2005 Ando
6,947,070 B2 9/2005 Takami
6,950,691 B2 9/2005 Uchikubo
6,956,703 B2 10/2005 Saito
6,967,673 B2 11/2005 Ozawa
6,977,670 B2 12/2005 Takahashi
6,980,227 B2 12/2005 Iida
6,982,740 B2 1/2006 Adair
6,985,170 B1 1/2006 Tsuyuki
6,992,694 B2 1/2006 Abe
6,995,786 B2 2/2006 Abe
6,997,871 B2 2/2006 Sonnenschein et al.
7,027,231 B2 4/2006 Miyano
7,030,904 B2 4/2006 Adair
7,037,258 B2 5/2006 Chatenever
7,042,488 B2 5/2006 Higuchi
7,043,153 B2 5/2006 Takeyama
7,046,270 B2 5/2006 Murata
7,050,086 B2 5/2006 Ozawa
7,074,181 B2 7/2006 Futatsugi
7,074,182 B2 7/2006 Rovegno
7,085,064 B2 8/2006 Uzawa
7,097,615 B2 8/2006 Banik
7,104,951 B2 9/2006 Hasegawa
7,108,656 B2 9/2006 Fujikawa
7,108,657 B2 9/2006 Irion et al.
7,119,830 B2 10/2006 Saito
7,123,288 B2 10/2006 Abe
7,128,709 B2 10/2006 Saruya
7,129,472 B1 10/2006 Okawa
7,133,063 B2 11/2006 Abe
D534,656 S 1/2007 Pilvisto
7,156,863 B2 1/2007 Sonnenschein
7,158,314 B2 1/2007 Fujii
7,179,221 B2 2/2007 Tsujita
7,180,686 B2 2/2007 Kato
7,218,454 B2 5/2007 Miyano
7,223,231 B2 5/2007 Akiba
7,231,135 B2 6/2007 Esenyan
7,232,409 B2 6/2007 Hale
7,233,820 B2 6/2007 Gilboa
7,242,833 B2 7/2007 Yang
7,248,281 B2 7/2007 Abe
7,248,296 B2 7/2007 Iketani

(56) References Cited

U.S. PATENT DOCUMENTS

| | | | |
|---|---|---|---|
| 7,252,633 | B2 | 8/2007 | Obata |
| 7,255,676 | B2 | 8/2007 | Higuchi |
| 7,262,797 | B2 | 8/2007 | Weldum |
| 7,267,647 | B2 | 9/2007 | Okada |
| 7,273,452 | B2 | 9/2007 | Barbato |
| 7,277,120 | B2 | 10/2007 | Gere |
| 7,280,140 | B2 | 10/2007 | Henderson |
| 7,280,283 | B1 | 10/2007 | Kasai |
| 7,282,025 | B2 | 10/2007 | Abe |
| 7,306,588 | B2 | 12/2007 | Loeb |
| 7,330,749 | B1 | 2/2008 | Bhunachet |
| D564,659 | S | 3/2008 | Hayashi |
| D564,660 | S | 3/2008 | Hayashi |
| 7,351,202 | B2 | 4/2008 | Long |
| 7,355,625 | B1 | 4/2008 | Mochida |
| 7,358,987 | B2 | 4/2008 | Takeshige |
| 7,365,768 | B1 | 4/2008 | Ono |
| 7,371,211 | B2 | 5/2008 | Akiba |
| 7,379,252 | B2 | 5/2008 | Murayama |
| 7,384,308 | B2 | 6/2008 | Boehnlein et al. |
| 7,399,304 | B2 | 7/2008 | Gambale |
| 7,400,341 | B2 | 7/2008 | Abe |
| 7,401,984 | B2 | 7/2008 | Pattie |
| 7,409,130 | B2 | 8/2008 | Hatori |
| 7,420,586 | B2 | 9/2008 | Higuchi |
| 7,427,263 | B2 | 9/2008 | Hoeg |
| 7,431,619 | B2 | 10/2008 | Boehnlein et al. |
| 7,435,217 | B2 | 10/2008 | Wiklof |
| 7,435,218 | B2 | 10/2008 | Krattiger |
| 7,440,005 | B2 | 10/2008 | Enomoto |
| 7,443,488 | B2 | 10/2008 | Ogawa |
| 7,450,151 | B2 | 11/2008 | Kaneko |
| 7,466,490 | B2 | 12/2008 | Igarashi |
| 7,471,310 | B2 | 12/2008 | Amling |
| 7,484,709 | B2 | 2/2009 | Efinger |
| 7,486,449 | B2 | 2/2009 | Miyano |
| 7,492,388 | B2 | 2/2009 | Odlivak |
| 7,514,667 | B2 | 4/2009 | Matsumoto |
| 7,518,632 | B2 | 4/2009 | Konomura |
| 7,530,948 | B2 | 5/2009 | Seibel |
| 7,542,069 | B2 | 6/2009 | Tashiro |
| 7,553,276 | B2 | 6/2009 | Iddan |
| 7,559,889 | B2 | 7/2009 | Takahashi |
| 7,559,892 | B2 | 7/2009 | Adler |
| 7,561,351 | B2 | 7/2009 | Konno |
| 7,569,012 | B2 | 8/2009 | Tanaka |
| 7,573,499 | B2 | 8/2009 | Doguchi |
| 7,576,310 | B2 | 8/2009 | Konno |
| 7,581,988 | B2 | 9/2009 | Boehnlein et al. |
| 7,582,055 | B2 | 9/2009 | Komiya |
| 7,582,056 | B2 | 9/2009 | Noguchi |
| 7,584,534 | B2 | 9/2009 | Pease et al. |
| 7,585,274 | B2 | 9/2009 | Homma |
| 7,588,535 | B2 | 9/2009 | Adler |
| 7,593,051 | B2 | 9/2009 | Suda |
| 7,621,868 | B2 | 11/2009 | Breidenthal |
| 7,621,869 | B2 | 11/2009 | Ratnakar |
| 7,623,150 | B2 | 11/2009 | Kobayashi |
| 7,627,189 | B2 | 12/2009 | Donomae |
| 7,630,148 | B1 | 12/2009 | Yang |
| 7,671,888 | B2 | 3/2010 | Nogami |
| 7,683,927 | B2 | 3/2010 | Higuchi |
| 7,695,429 | B2 | 4/2010 | Hino |
| 7,699,772 | B2 | 4/2010 | Pauker et al. |
| 7,701,650 | B2 | 4/2010 | Lin |
| 7,725,013 | B2 | 5/2010 | Sugimoto |
| 7,728,867 | B2 | 6/2010 | Fukuyama |
| 7,734,160 | B2 | 6/2010 | Sudo |
| 7,746,566 | B2 | 6/2010 | Mizusawa |
| 7,746,572 | B2 | 6/2010 | Asami |
| 7,749,156 | B2 | 7/2010 | Ouchi |
| 7,749,159 | B2 | 7/2010 | Crowley |
| 7,758,495 | B2 | 7/2010 | Pease et al. |
| 7,758,499 | B2 | 7/2010 | Adler |
| 7,772,786 | B2 | 8/2010 | Hosoda |
| 7,773,110 | B2 | 8/2010 | Abe |
| 7,773,122 | B2 | 8/2010 | Irian |
| 7,773,318 | B2 | 8/2010 | Takato |
| 7,775,971 | B2 | 8/2010 | Fujimori |
| 7,775,973 | B2 | 8/2010 | Okada |
| 7,789,822 | B2 | 9/2010 | Suzuki |
| 7,800,656 | B2 | 9/2010 | Takeuchi |
| RE41,807 | E | 10/2010 | Yokoi |
| 7,821,529 | B2 | 10/2010 | Mochida |
| 7,837,614 | B2 | 11/2010 | Segawa |
| 7,841,880 | B2 | 11/2010 | Ikeda |
| 7,846,090 | B2 | 12/2010 | Pilvisto |
| 7,852,513 | B2 | 12/2010 | Donomae |
| 7,893,956 | B2 | 2/2011 | Ayrenschmalz |
| 7,896,802 | B2 | 3/2011 | Otawara |
| 7,901,352 | B2 | 3/2011 | Minami |
| 7,907,168 | B2 | 3/2011 | Eino |
| 7,907,170 | B2 | 3/2011 | Watanabe |
| 7,907,352 | B2 | 3/2011 | Miyano |
| 7,914,443 | B2 | 3/2011 | Uchimura |
| 7,918,788 | B2 | 4/2011 | Lin |
| 7,938,773 | B2 | 5/2011 | Kawai |
| 7,940,296 | B2 | 5/2011 | Ogino |
| 7,942,814 | B2 | 5/2011 | Remijan |
| 7,951,068 | B2 | 5/2011 | Kura |
| 7,967,745 | B2 | 6/2011 | Gilad |
| 7,976,462 | B2 * | 7/2011 | Wright ............... A61B 1/00096 600/171 |
| 7,995,093 | B2 | 8/2011 | Takeuchi |
| 7,998,064 | B2 | 8/2011 | Otawara |
| 8,002,696 | B2 | 8/2011 | Suzuki |
| 8,027,101 | B2 | 9/2011 | Suda |
| 8,033,992 | B2 | 10/2011 | Hino |
| 8,035,684 | B2 | 10/2011 | Wakito |
| 8,038,600 | B2 | 10/2011 | Uchiyama |
| 8,043,207 | B2 | 10/2011 | Adams |
| 8,060,172 | B2 | 11/2011 | Ishihara |
| 8,063,962 | B2 | 11/2011 | Hagihara |
| 8,066,631 | B2 | 11/2011 | Wimmer |
| 8,072,483 | B2 | 12/2011 | Tomioka |
| 8,072,537 | B2 | 12/2011 | Schwarz |
| 8,072,693 | B2 | 12/2011 | Togino |
| 8,075,477 | B2 | 12/2011 | Nakamura |
| 8,075,478 | B2 | 12/2011 | Campos |
| 8,098,441 | B2 | 1/2012 | Sasamoto |
| 8,100,920 | B2 | 1/2012 | Gambale |
| 8,102,415 | B2 | 1/2012 | Iriyama |
| 8,105,233 | B2 | 1/2012 | AbouElKheir |
| 8,113,846 | B2 | 2/2012 | Wallaker |
| 8,125,514 | B2 | 2/2012 | Sekiguchi |
| 8,125,515 | B2 | 2/2012 | Hibi |
| 8,130,454 | B2 | 3/2012 | Noguchi |
| 8,135,192 | B2 | 3/2012 | Matsuzaki |
| 8,135,454 | B2 | 3/2012 | Daniels |
| 8,139,296 | B2 | 3/2012 | Ito |
| 8,144,191 | B2 | 3/2012 | Kawanishi |
| 8,149,274 | B2 | 4/2012 | Yamazaki |
| 8,152,718 | B2 | 4/2012 | Cheng |
| 8,152,821 | B2 | 4/2012 | Gambale |
| 8,157,798 | B2 | 4/2012 | Takahashi |
| 8,164,836 | B2 | 4/2012 | Uzawa |
| 8,167,791 | B2 | 5/2012 | Tanaka |
| 8,167,795 | B2 | 5/2012 | Hoeg |
| 8,167,796 | B2 | 5/2012 | Negishi |
| 8,182,419 | B2 | 5/2012 | Kohno |
| 8,187,171 | B2 | 5/2012 | Irion |
| 8,187,174 | B2 | 5/2012 | Wang |
| 8,189,041 | B2 | 5/2012 | Konishi |
| 8,189,062 | B2 | 5/2012 | Irion |
| 8,194,380 | B2 | 6/2012 | Murata |
| 8,197,400 | B2 | 6/2012 | Boutillette |
| 8,200,042 | B2 | 6/2012 | Doi |
| 8,208,015 | B2 | 6/2012 | Unsai |
| 8,211,009 | B2 | 7/2012 | Tanaka |
| 8,212,862 | B2 | 7/2012 | Kase |
| 8,212,863 | B2 | 7/2012 | Tanaka |
| 8,221,309 | B2 | 7/2012 | Iida |
| 8,221,311 | B2 | 7/2012 | Campos |
| 8,223,198 | B2 | 7/2012 | Shibasaki |

(56) References Cited

U.S. PATENT DOCUMENTS 8,228,369 B2 7/2012 Kojima
8,229,549 B2 7/2012 Whitman
8,235,942 B2 8/2012 Frassica
8,248,414 B2 8/2012 Gattani
8,262,558 B2 9/2012 Sato
8,262,565 B2 9/2012 Okada
8,279,275 B2 10/2012 Gono
8,295,566 B2 10/2012 Nishimura
8,300,325 B2 10/2012 Katahira
8,310,529 B2 11/2012 Krupnick
8,334,900 B2 12/2012 Qu
8,345,092 B2 1/2013 Takasaki
8,348,835 B2 1/2013 Fujimori
8,360,960 B2 1/2013 Sasaki
8,360,964 B2 1/2013 Ertas
8,366,623 B2 2/2013 Misono
8,382,673 B2 2/2013 Nagano
8,394,013 B2 3/2013 Ichimura
8,394,014 B2 3/2013 Fuerst
8,425,405 B2 4/2013 Mitani
8,435,173 B2 5/2013 Hosaka
8,439,829 B2 5/2013 Miyamoto
8,444,547 B2 5/2013 Miyamoto
8,444,548 B2 5/2013 Kumei
8,449,456 B2 5/2013 Ueno
8,449,457 B2 5/2013 Aizenfeld
8,456,562 B2 6/2013 Ishii
8,460,182 B2 6/2013 Ouyang
8,465,421 B2 6/2013 Finkman
8,480,670 B2 7/2013 Sugita
8,491,467 B2 7/2013 Miyamoto
8,520,919 B2 8/2013 Stepp
8,523,764 B2 9/2013 Hatcher
8,523,766 B2 9/2013 Kudoh
8,764,642 B2 7/2014 Bendele
9,144,373 B2 9/2015 Kaye
2002/0007110 A1 1/2002 Irion
2002/0087047 A1 7/2002 Remijan
2002/0098732 A1 7/2002 Shimizu
2002/0109771 A1* 8/2002 Ledbetter ............... H04N 7/108 348/14.09
2002/0109774 A1 8/2002 Meron
2002/0151768 A1 10/2002 Akiba
2002/0161281 A1 10/2002 Jaffe
2002/0161282 A1 10/2002 Fulghum
2002/0183591 A1 12/2002 Matsuura
2003/0030918 A1 2/2003 Murayama
2003/0032860 A1 2/2003 Avni
2003/0036681 A1 2/2003 Aviv
2003/0055314 A1 3/2003 Petitto
2003/0083552 A1 5/2003 Remijan
2003/0125788 A1 7/2003 Long
2003/0130564 A1 7/2003 Martone
2003/0139648 A1 7/2003 Foley
2003/0158462 A1 8/2003 Takase
2003/0181787 A1 9/2003 Kondo
2003/0199860 A1 10/2003 Loeb
2004/0015049 A1 1/2004 Zaar
2004/0019347 A1 1/2004 Sakurai
2004/0024290 A1 2/2004 Root
2004/0034311 A1 2/2004 Mihalcik
2004/0073120 A1 4/2004 Motz
2004/0104999 A1 6/2004 Okada
2004/0111012 A1 6/2004 Whitman
2004/0133076 A1 7/2004 Kobayashi
2004/0138532 A1 7/2004 Glukhovsky
2004/0143162 A1 7/2004 Krattiger
2004/0158129 A1 8/2004 Okada
2004/0160682 A1 8/2004 Miyano
2004/0176661 A1 9/2004 Futatsugi
2004/0190159 A1 9/2004 Hasegawa
2004/0210113 A1 10/2004 Hasegawa
2004/0220451 A1 11/2004 Gravenstein
2004/0242958 A1 12/2004 Fujikawa
2004/0242961 A1 12/2004 Bughici
2004/0249247 A1* 12/2004 Iddan ........................... 600/170
2004/0254423 A1 12/2004 Wendlandt
2004/0267093 A1 12/2004 Miyagi et al.
2005/0020876 A1 1/2005 Shioda et al.
2005/0027164 A1 2/2005 Barbato
2005/0038317 A1 2/2005 Ratnakar
2005/0038318 A1 2/2005 Goldwasser
2005/0043583 A1 2/2005 Killmann et al.
2005/0080342 A1 4/2005 Gilreath et al.
2005/0090709 A1 4/2005 Okada
2005/0096501 A1* 5/2005 Stelzer et al. ................ 600/101
2005/0154255 A1 7/2005 Jacobs
2005/0154262 A1 7/2005 Banik
2005/0182295 A1 8/2005 Soper
2005/0203338 A1 9/2005 Couvillon, Jr. et al.
2005/0234296 A1 10/2005 Saadat
2005/0234347 A1 10/2005 Yamataka
2005/0251127 A1 11/2005 Brosch
2005/0256376 A1 11/2005 Bar-Or
2005/0261553 A1 11/2005 Swain
2005/0272975 A1 12/2005 McWeeney
2005/0283048 A1 12/2005 Gill
2005/0284491 A1 12/2005 Tashiro
2006/0047184 A1 3/2006 Banik
2006/0052663 A1 3/2006 Koitabashi
2006/0063976 A1 3/2006 Aizenfeld et al.
2006/0069307 A1 3/2006 Boulais
2006/0069314 A1 3/2006 Farr
2006/0149129 A1 7/2006 Watts et al.
2006/0173244 A1 8/2006 Boulais
2006/0183971 A1 8/2006 Haviv
2006/0183975 A1 8/2006 Saadat
2006/0189845 A1 8/2006 Maahs
2006/0211916 A1 9/2006 Kasahara
2006/0217594 A1 9/2006 Ferguson
2006/0224040 A1 10/2006 Khait
2006/0229499 A1 10/2006 Eisenkolb
2006/0241347 A1 10/2006 Whitehead
2006/0252994 A1* 11/2006 Ratnakar ............ A61B 1/00179 600/173
2006/0264704 A1 11/2006 Fujimori
2006/0293556 A1 12/2006 Garner
2006/0293562 A1 12/2006 Uchimura
2007/0015964 A1 1/2007 Eversull
2007/0015968 A1 1/2007 Shelnutt
2007/0019916 A1 1/2007 Takami
2007/0020694 A1 1/2007 Pickford
2007/0030345 A1 2/2007 Amling
2007/0049803 A1 3/2007 Moriyama
2007/0055100 A1 3/2007 Kato
2007/0073109 A1 3/2007 Irion
2007/0078304 A1 4/2007 Shimizu
2007/0083081 A1 4/2007 Schlagenhauf
2007/0100206 A1 5/2007 Lin
2007/0106119 A1 5/2007 Hirata
2007/0115376 A1 5/2007 Igarashi
2007/0118019 A1 5/2007 Mitani
2007/0123748 A1 5/2007 Meglan
2007/0142711 A1 6/2007 Bayer et al.
2007/0162095 A1 7/2007 Kimmel
2007/0167673 A1 7/2007 Enomoto
2007/0167681 A1 7/2007 Gill
2007/0173686 A1 7/2007 Lin
2007/0173687 A1 7/2007 Shima
2007/0177008 A1 8/2007 Bayer et al.
2007/0177009 A1 8/2007 Bayer et al.
2007/0185384 A1 8/2007 Bayer et al.
2007/0197875 A1* 8/2007 Osaka ................ A61B 1/00096 600/173
2007/0203396 A1* 8/2007 McCutcheon et al. ....... 600/173
2007/0206945 A1 9/2007 Delorme
2007/0208225 A1 9/2007 Czaniera
2007/0213590 A1 9/2007 Squicciarini
2007/0213591 A1 9/2007 Aizenfeld
2007/0225556 A1 9/2007 Ortiz et al.
2007/0225565 A1 9/2007 Ogino
2007/0229656 A1 10/2007 Khait
2007/0244353 A1* 10/2007 Larsen .......................... 600/105
2007/0244362 A1 10/2007 El-Hachem

(56) References Cited

U.S. PATENT DOCUMENTS

2007/0244366 A1 10/2007 Murata
2007/0249899 A1 10/2007 Seifert
2007/0265498 A1 11/2007 Ito
2007/0282165 A1 12/2007 Hopkins
2007/0293720 A1 12/2007 Bayer
2008/0009672 A1 1/2008 Krattiger
2008/0021274 A1 1/2008 Bayer et al.
2008/0021281 A1 1/2008 Fujimori
2008/0039689 A1 2/2008 Yoshimitsu
2008/0039693 A1 2/2008 Karasawa
2008/0045797 A1 2/2008 Yasushi
2008/0051628 A1 2/2008 Pecherer
2008/0051629 A1 2/2008 Sugiyama et al.
2008/0051655 A1 2/2008 Sato
2008/0058595 A1 3/2008 Snoke
2008/0058598 A1 3/2008 Ries
2008/0058601 A1 3/2008 Fujimori
2008/0064931 A1 3/2008 Schena
2008/0065127 A1 3/2008 Adams
2008/0071290 A1 3/2008 Larkin
2008/0100699 A1 5/2008 Hibi
2008/0130108 A1 6/2008 Bayer et al.
2008/0139881 A1 6/2008 Cover
2008/0163652 A1 7/2008 Shatskin
2008/0167529 A1 7/2008 Otawara
2008/0171910 A1 7/2008 Kanazawa
2008/0177139 A1 7/2008 Courtney
2008/0177140 A1 7/2008 Cline
2008/0188715 A1 8/2008 Fujimoto
2008/0225134 A1 9/2008 Amling
2008/0255425 A1 10/2008 Voegele
2008/0262302 A1 10/2008 Azarbarzin et al.
2008/0262312 A1 10/2008 Carroll et al.
2008/0312497 A1 12/2008 Elmouelhi
2009/0005643 A1 1/2009 Smith
2009/0054790 A1 2/2009 Czaniera
2009/0062615 A1 3/2009 Yamaya
2009/0086017 A1 4/2009 Miyano
2009/0093679 A1 4/2009 Suigetsu
2009/0118577 A9 5/2009 Snay
2009/0137869 A1 5/2009 Soutorine
2009/0147076 A1 6/2009 Ertas
2009/0161234 A1 6/2009 Sasamoto
2009/0163769 A1 6/2009 Robertson et al.
2009/0209811 A1 8/2009 Higuchi
2009/0216084 A1 8/2009 Yamane
2009/0231419 A1 9/2009 Bayer
2009/0247831 A1 10/2009 Miyamoto
2009/0253966 A1 10/2009 Ichimura
2009/0259097 A1 10/2009 Thompson
2009/0259102 A1 10/2009 Koninckx
2009/0268011 A1 10/2009 Scott
2009/0284649 A1 11/2009 Pease et al.
2009/0287047 A1 11/2009 Onoda
2009/0287192 A1 11/2009 Vivenzio
2009/0290236 A1 11/2009 Wang
2009/0299144 A1 12/2009 Shigemori
2009/0306474 A1 12/2009 Wilson
2009/0306476 A1 12/2009 Banik
2009/0318757 A1 12/2009 Singh
2010/0010301 A1 1/2010 Hale et al.
2010/0010302 A1 1/2010 Hadani
2010/0013914 A1 1/2010 Bettesh
2010/0016673 A1 1/2010 Bandy
2010/0030020 A1 2/2010 Sanders
2010/0042097 A1 2/2010 Newton
2010/0047733 A1 2/2010 Nahlieli
2010/0053312 A1* 3/2010 Watanabe et al. .............. 348/65
2010/0073470 A1 3/2010 Takasaki
2010/0076268 A1 3/2010 Takasugi
2010/0081874 A1 4/2010 Miyamoto et al.
2010/0081875 A1 4/2010 Fowler
2010/0087706 A1 4/2010 Syed
2010/0121142 A1 5/2010 Ouyang et al.
2010/0123950 A1 5/2010 Fujiwara
2010/0130822 A1 5/2010 Katayama
2010/0137682 A1 6/2010 Doguchi et al.
2010/0137687 A1 6/2010 Schwartz
2010/0141746 A1 6/2010 Ikeda
2010/0152612 A1 6/2010 Headley
2010/0160729 A1 6/2010 Smith
2010/0174144 A1 7/2010 Hsu
2010/0185056 A1 7/2010 Gordon
2010/0187408 A1 7/2010 Klem
2010/0201985 A1 8/2010 Wang
2010/0204609 A1 8/2010 Worth
2010/0217076 A1 8/2010 Ratnakar
2010/0217081 A1 8/2010 Deppmeier
2010/0228086 A1 9/2010 Ohki
2010/0245653 A1 9/2010 Bodor
2010/0249496 A1 9/2010 Cardenas
2010/0249513 A1 9/2010 Tydlaska
2010/0256447 A1 10/2010 Dubi
2010/0286475 A1 11/2010 Robertson
2010/0296178 A1 11/2010 Genet
2010/0298640 A1 11/2010 Oneda
2010/0298773 A1 11/2010 Nitsan
2010/0305503 A1 12/2010 Fang et al.
2010/0317919 A1 12/2010 Takaoka
2010/0317921 A1 12/2010 Marple
2010/0318061 A1 12/2010 Derrick
2011/0028790 A1 2/2011 Farr
2011/0054256 A1 3/2011 Cushner
2011/0112363 A1 5/2011 Koga et al.
2011/0160530 A1 6/2011 Ratnakar
2011/0169931 A1 7/2011 Pascal
2011/0184243 A1 7/2011 Wright
2011/0196200 A1 8/2011 Glozman
2011/0196204 A1 8/2011 Setty
2011/0211267 A1 9/2011 Takato
2011/0224487 A1 9/2011 Ogawa
2011/0245600 A1 10/2011 Ishii
2011/0245609 A1 10/2011 Laser
2011/0257478 A1 10/2011 Kleiner
2011/0263938 A1 10/2011 Levy
2011/0282144 A1 11/2011 Gettman
2011/0282148 A1 11/2011 Kase
2011/0288374 A1 11/2011 Hadani
2011/0295061 A1 12/2011 Haramaty
2011/0295062 A1 12/2011 GratacosSolsona
2011/0295064 A1 12/2011 Kagawa
2011/0306832 A1 12/2011 Bassan
2011/0313249 A1 12/2011 Viola
2012/0010465 A1 1/2012 Erikawa et al.
2012/0029291 A1 2/2012 Wallace
2012/0040305 A1 2/2012 Karazivan
2012/0041534 A1 2/2012 Clerc
2012/0046524 A1 2/2012 Miyamoto
2012/0053407 A1 3/2012 Levy
2012/0057251 A1 3/2012 Takato
2012/0065468 A1 3/2012 Levy et al.
2012/0071748 A1 3/2012 Mark
2012/0078042 A1 3/2012 Uram
2012/0088965 A1 4/2012 Stokes
2012/0095391 A1 4/2012 Bendele
2012/0104230 A1 5/2012 Eismann
2012/0178995 A1 7/2012 Newton
2012/0209062 A1 8/2012 Qiao
2012/0229615 A1 9/2012 Kirma
2012/0232340 A1 9/2012 Levy
2012/0232342 A1 9/2012 Reydel
2012/0232343 A1 9/2012 Levy
2012/0253121 A1 10/2012 Kitano
2012/0253284 A1 10/2012 Nitsan
2012/0259175 A1 10/2012 Reydel
2012/0265094 A1 10/2012 Goldfarb
2013/0012778 A1 1/2013 Bayer
2013/0012794 A1 1/2013 Zeng
2013/0060086 A1 3/2013 Talbert
2013/0109916 A1 5/2013 Levy
2013/0109918 A1 5/2013 Pagan
2013/0110003 A1 5/2013 Surti
2013/0131445 A1 5/2013 Zerfas
2013/0131447 A1 5/2013 Benning

(56) References Cited

U.S. PATENT DOCUMENTS

| | | | |
|---|---|---|---|
| 2013/0131454 | A1 | 5/2013 | McCormack |
| 2013/0137930 | A1 | 5/2013 | Menabde |
| 2013/0172670 | A1 | 7/2013 | Levy |
| 2013/0172673 | A1 | 7/2013 | Kennedy |
| 2013/0172674 | A1 | 7/2013 | Kennedy |
| 2013/0172677 | A1 | 7/2013 | Kennedy |
| 2013/0172678 | A1 | 7/2013 | Kennedy |
| 2013/0190561 | A1 | 7/2013 | Oskin |
| 2013/0194404 | A1 | 8/2013 | Christiansen |
| 2013/0204088 | A1 | 8/2013 | Miyamoto |
| 2013/0253272 | A1 | 9/2013 | Takahashi |
| 2013/0267778 | A1 | 10/2013 | Rehe |
| 2013/0296649 | A1 | 11/2013 | Kirma |
| 2013/0314521 | A1 | 11/2013 | Satake |
| 2013/0317295 | A1 | 11/2013 | Morse |
| 2014/0364691 | A1 | 12/2014 | Krivopisk |

FOREIGN PATENT DOCUMENTS

| | | | |
|---|---|---|---|
| CN | 1988841 | | 6/2007 |
| CN | 2936129 | Y | 8/2007 |
| CN | 101061940 | A | 10/2007 |
| CN | 201108422 | Y | 9/2008 |
| CN | 101385633 | A | 3/2009 |
| CN | 101396258 | | 4/2009 |
| CN | 101926171 | | 12/2010 |
| CN | 102058375 | A | 5/2011 |
| CN | 102058380 | A | 5/2011 |
| CN | 101061940 | | 6/2011 |
| CN | 201870615 | U | 6/2011 |
| CN | 102469924 | | 5/2012 |
| DE | 102005008153 | A1 | 11/2005 |
| EP | 0029555 | A2 | 6/1981 |
| EP | 543738 | A1 | 5/1993 |
| EP | 730844 | | 9/1996 |
| EP | 1195630 | A2 | 4/2002 |
| EP | 1325458 | | 7/2003 |
| EP | 1347702 | A2 | 10/2003 |
| EP | 948283 | B1 | 4/2004 |
| EP | 1535565 | | 6/2005 |
| EP | 1073365 | B1 | 7/2005 |
| EP | 1627595 | A1 | 2/2006 |
| EP | 668738 | B1 | 6/2006 |
| EP | 1685790 | A1 | 8/2006 |
| EP | 1472972 | B1 | 10/2006 |
| EP | 1790280 | A1 | 5/2007 |
| EP | 1834572 | A1 | 9/2007 |
| EP | 1952750 | | 8/2008 |
| EP | 1977675 | | 10/2008 |
| EP | 1977682 | A2 | 10/2008 |
| EP | 1974000653 | | 10/2008 |
| EP | 1992292 | A1 | 11/2008 |
| EP | 2022389 | A1 | 2/2009 |
| EP | 2144571 | A2 | 1/2010 |
| EP | 2276389 | A1 | 1/2011 |
| EP | 1835847 | B1 | 5/2011 |
| EP | 1870014 | B1 | 1/2012 |
| EP | 2501271 | A1 | 9/2012 |
| EP | 2503933 | A1 | 10/2012 |
| EP | 2512577 | A2 | 10/2012 |
| EP | 2529660 | A1 | 12/2012 |
| EP | 2596756 | A1 | 5/2013 |
| EP | 2623019 | A1 | 8/2013 |
| GB | 2321132 | | 7/1998 |
| GB | 2352922 | A | 2/2001 |
| JP | 55078932 | | 6/1980 |
| JP | 61055657 | | 11/1986 |
| JP | 6359332 | | 11/1988 |
| JP | H02188709 | A | 7/1990 |
| JP | 5049000594 | | 3/1993 |
| JP | H05309069 | | 11/1993 |
| JP | 6105000800 | | 4/1994 |
| JP | 7000000352 | | 1/1995 |
| JP | 8122000657 | | 5/1996 |
| JP | 1013007179 | | 4/1998 |
| JP | 1015001113 | | 6/1998 |
| JP | 11125773 | | 5/1999 |
| JP | 11137512 | | 5/1999 |
| JP | H11125773 | A | 5/1999 |
| JP | 1116009340 | | 6/1999 |
| JP | 1116009341 | | 6/1999 |
| JP | H11253401 | | 9/1999 |
| JP | 2000171727 | A | 6/2000 |
| JP | 2000330015 | A | 11/2000 |
| JP | 2001061762 | | 3/2001 |
| JP | 2001198086 | | 7/2001 |
| JP | 2002000559 | | 1/2002 |
| JP | 2002017667 | | 1/2002 |
| JP | 2002058636 | | 2/2002 |
| JP | 200265589 | A | 3/2002 |
| JP | 2002065575 | | 3/2002 |
| JP | 2002078675 | | 3/2002 |
| JP | 2002216902 | | 8/2002 |
| JP | 2002291693 | | 10/2002 |
| JP | 2003038431 | | 2/2003 |
| JP | 2003061900 | | 3/2003 |
| JP | 2003111724 | | 4/2003 |
| JP | 2003190082 | | 7/2003 |
| JP | 2003220017 | | 8/2003 |
| JP | 2003245247 | | 9/2003 |
| JP | 2004022391 | | 1/2004 |
| JP | 2004049754 | | 2/2004 |
| JP | 2004049756 | | 2/2004 |
| JP | 2004129834 | | 4/2004 |
| JP | 2004205779 | A | 7/2004 |
| JP | 2005013557 | A | 1/2005 |
| JP | 2005058547 | | 3/2005 |
| JP | 2005253543 | | 9/2005 |
| JP | 2005323874 | A | 11/2005 |
| JP | 3765500 | | 2/2006 |
| JP | 2006068109 | A | 3/2006 |
| JP | 2006218155 | | 8/2006 |
| JP | 2006280954 | | 10/2006 |
| JP | 2006288758 | | 10/2006 |
| JP | 2007020866 | A | 2/2007 |
| JP | 2007185276 | | 7/2007 |
| JP | 2008068025 | | 3/2008 |
| JP | 2008118568 | | 5/2008 |
| JP | 2008161569 | A | 7/2008 |
| JP | 2008229204 | | 10/2008 |
| JP | 2008257108 | A | 10/2008 |
| JP | 2009233186 | | 10/2009 |
| JP | 4445647 | | 4/2010 |
| JP | 2010178766 | A | 8/2010 |
| JP | 2010279539 | | 12/2010 |
| WO | 92/19148 | A1 | 11/1992 |
| WO | 00/052643 | A1 | 9/2000 |
| WO | 2002045595 | | 6/2002 |
| WO | 2004026125 | | 4/2004 |
| WO | 2005082228 | A1 | 9/2005 |
| WO | 2006073581 | | 7/2006 |
| WO | 20061105932 | A1 | 10/2006 |
| WO | 2007087421 | | 8/2007 |
| WO | 2007113801 | A2 | 10/2007 |
| WO | 2007/136859 | A2 | 11/2007 |
| WO | 2008/012813 | A1 | 1/2008 |
| WO | 2008073243 | | 6/2008 |
| WO | 2008093288 | | 8/2008 |
| WO | 2008139770 | | 11/2008 |
| WO | 2008155776 | | 12/2008 |
| WO | 2008156623 | | 12/2008 |
| WO | 2009009414 | | 1/2009 |
| WO | 2009025843 | | 2/2009 |
| WO | 2009040744 | | 4/2009 |
| WO | 2009095915 | | 8/2009 |
| WO | 2010021342 | | 2/2010 |
| WO | 2010028612 | | 3/2010 |
| WO | 2010045406 | | 4/2010 |
| WO | 2010064506 | | 6/2010 |
| WO | 2010066788 | | 6/2010 |
| WO | 2010146587 | | 12/2010 |
| WO | 2010146587 | A1 | 12/2010 |
| WO | 2011008922 | | 1/2011 |
| WO | 2011041724 | | 4/2011 |

(56) References Cited

FOREIGN PATENT DOCUMENTS

| | | | |
|---|---|---|---|
| WO | 2011083451 | | 7/2011 |
| WO | 2011126812 | | 10/2011 |
| WO | 2012038958 | | 3/2012 |
| WO | 2013131578 | | 3/2012 |
| WO | 2012056453 | | 5/2012 |
| WO | 2012077116 | | 6/2012 |
| WO | 2012077117 | | 6/2012 |
| WO | 2012088201 | A2 | 6/2012 |
| WO | 2012103266 | | 8/2012 |
| WO | 2012120507 | | 9/2012 |
| WO | 2012153324 | | 11/2012 |
| WO | 2013014673 | | 1/2013 |
| WO | 2013024476 | | 2/2013 |
| WO | 2013043704 | | 3/2013 |
| WO | 2013128136 | | 9/2013 |
| WO | 2013144944 | | 10/2013 |
| WO | 2014061023 | | 4/2014 |

OTHER PUBLICATIONS

International Search Report for PCT/EP2009/066726, dated Aug. 16, 2010.
Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
International Search Report for PCT/IL2011/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL10/00476 dated Sep. 27, 2010, 2 pages.
International Search Report of PCT/IL2011/000745, dated May 8, 2012.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; dated Jul. 26, 2011 through Jun. 17, 2015.
Notice of Allowance dated Jun. 17, 2015 for U.S. Appl. No. 13/190,968.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action for Japanese Patent Application No. JP2014-522214, dated Apr. 26, 2016.
Office Action for Japanese Patent Application No. JP2014-525562, dated Apr. 26, 2016.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Supplementary European Search Report for EP118471911, dated Jan. 16, 2015.
Examination Search Report for Canadian Patent Application No. CA2765559, dated Jan. 18, 2016.
Office Action dated Aug. 4, 2015 for U.S. Appl. No. 13/557,114.
Office Action dated Nov. 16, 2015 for U.S. Appl. No. 13/557,114.
Office Action for Chinese Patent Application No. 201280038808.8, dated May 20, 2015.
Second Office Action for Chinese Patent Applicatio No. CN201280038808.8, dated Feb. 25, 2016.
Office Action dated Aug. 6, 2015 for U.S. Appl. No. 13/119,032.
First Office Action for CN 2012800368972, dated Jun. 1, 2015.
Examination Report for Canadian Patent Application No. CA2765559, dated Jan. 18, 2016.
Corrected European Search Opinion for EP14186113.8, dated Apr. 29, 2015.
Extended European Search Report for EP12817452.1, dated Mar. 9, 2015.
Office Action dated Aug. 19, 2015 for U.S. Appl. No. 13/713,466.
Office Action dated Jul. 21, 2015 for U.S. Appl. No. 13/992,021.
Office Action dated Aug. 5, 2015 for U.S. Appl. No. 13/212,627.
Office Action for Chinese Patent Application No. 201180067259.2, dated May 29, 2015.
Office Action dated Aug. 18, 2015 for U.S. Appl. No. 13/713,449.
First office action for CN2011800627366, dated Feb. 25, 2015.
Supplementary European Search Report for European Application No. EP12823972, dated May 13, 2015.
Extended European Search Report for EP14186113.8, dated Apr. 1, 2015.
Notice of Allowance dated Dec. 15, 2014 for U.S. Appl. No. 13/713,466.
Notice of Allowance dated Dec. 15, 2015 for U.S. Appl. No. 13/713,466.
Office Action dated Jan. 12, 2016 for U.S. Appl. No. 13/713,466.
Office Action for Japanese Patent Application No. 2013-542668, dated Oct. 1, 2015.
Office Action for Japanese Patent Application No. 2013-535586, dated Sep. 24, 2015.
Second office action for Chinese Patent Application No. 201180062736.6, dated Oct. 12, 2015.
Notice of Allowance dated Dec. 23, 2015 for U.S. Appl. No. 13/992,021.
Office Action dated Dec. 4, 2015 for U.S. Appl. No. 13/822,908.
Office Action dated Nov. 24, 2015 for U.S. Appl. No. 13/413,059.
Office Action dated Nov. 3, 2015 for U.S. Appl. No. 13/992,014.
Office Action dated Oct. 7, 2015 for U.S. Appl. No. 13/882,004.
Extended European Search Report for EP11846069.0, dated Apr. 24, 2014.
First Office Action for Chinese Patent Applicatio No. CN201380053351.2, dated Mar. 2, 2016.

* cited by examiner

MULTI-CAMERA ENDOSCOPE

CROSS REFERENCE TO RELATED APPLICATIONS

This application is a continuation-in-part (CIP) of U.S. patent application Ser. No. 13/119,032, filed Jul. 15, 2011 which is a national phase application with the U.S. Patent and Trademark Office of International Patent Application No. PCT/IL2010/000476, filed Jun. 16, 2010, which claims the benefit of U.S. Provisional Patent Application No. 61/218,085, filed Jun. 18, 2009, which are incorporated herein by reference in their entirety.

FIELD

Embodiments of the disclosure relate to a multi-camera endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, according to some embodiments, a tip section of a multi-camera endoscope, the tip section comprising a front-pointing camera and a discrete front illuminator associated therewith, two or more side-pointing cameras positioned at or in proximity to a distal end of the tip section, wherein each of the two or more side-pointing cameras having a discrete side illuminator associated therewith; and a working channel configured for insertion of a surgical tool.

There is further provided, according to some embodiments, a multi-camera endoscope comprising an elongated shaft terminating with a tip section turnable by way of a bending section, wherein the tip section comprises a front-pointing camera and a discrete front illuminator associated therewith, two or more side-pointing cameras positioned at or in proximity to a distal end of the tip section, wherein each of the two or more side-pointing cameras having a discrete side illuminator associated therewith, and a working channel configured for insertion of a surgical tool.

The tip section may further include a pathway fluid injector for inflating and/or cleaning a body cavity into which the endoscope is inserted.

The tip section may further include a fluid injector configured for cleaning the front-pointing camera and/or the discrete front illuminator. The tip section may further include two or more side fluid injectors configured for cleaning the two or more side-pointing cameras and/or the discrete side illuminators.

The tip section may include two side-pointing cameras. The tip section may further include two side-pointing cameras pointing at directions essentially opposing to one another.

The tip section may further include three or more (for example, three, four, five, six or more) side-pointing cameras positioned essentially at equal distances from each other along the perimeter of the tip section.

According to some embodiments, the discrete front illuminator may include a light-emitting diode (LED). According to some embodiments, each of the discrete side illuminators may include a light-emitting diode (LED). According to some embodiments, each of the discrete front and side illuminators may include a light-emitting diode (LED).

There is provided, according to some embodiments, a tip section of a multi-camera endoscope, the tip section comprising: two or more side-pointing cameras positioned at or in proximity to a distal end of the tip section, wherein the field of view provided by the two or more side-pointing cameras covers a front and side views; one or more discrete illuminator; a working channel configured for insertion of a surgical tool; and a pathway fluid injector for inflating and/or cleaning a body cavity into which the endoscope is inserted.

There is provided, according to some embodiments, a tip section of a multi-camera endoscope, the tip section comprising: three side-pointing cameras positioned at or in proximity to a distal end of the tip section, wherein the field of view provided by the three side-pointing cameras covers a front and side views; one or more discrete illuminator; a working channel configured for insertion of a surgical tool; and a pathway fluid injector for inflating and/or cleaning a body cavity into which the endoscope is inserted.

There is provided, according to some embodiments, a tip section of a multi-camera endoscope, the tip section comprising: three side-pointing cameras positioned at or in proximity to a distal end of the tip section, wherein the field of view provided by the three side-pointing cameras covers a front and side views; three discrete illuminators (such as LEDs), each associated with each one of the three side-pointing cameras; and a working channel configured for insertion of a surgical tool.

There is provided, according to some embodiments, a tip section of a multi-camera endoscope, the tip section comprising: three side-pointing cameras positioned at or in proximity to a distal end of the tip section, wherein the field of view provided by the three side-pointing cameras covers a front and side views; one front discrete illuminator (such as a LED), and a working channel configured for insertion of a surgical tool.

The tip section may further include a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein the tip section comprises: two or more side-pointing cameras positioned at or in proximity to a distal end of the tip section, wherein the field of view provided by the two or more side-pointing cameras covers a front and side views; one or more discrete illuminator; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein the tip section comprises: three side-pointing cameras positioned at or in proximity to a distal end of the tip section, wherein the field of view provided by the three side-pointing cameras covers a front and side views; three discrete illuminators (such as LEDs), each associated with each one of the three side-pointing cameras, and a working channel configured for insertion of a surgical tool.

There is provided, according to some embodiments, a multi-camera endoscope comprising: an elongated shaft terminating with a tip section turnable by way of a bending section, wherein the tip section comprises: three side-pointing cameras positioned at or in proximity to a distal end of the tip section, wherein the field of view provided by the three side-pointing cameras covers a front and side views; one front discrete illuminator (such as a LED), and a working channel configured for insertion of a surgical tool.

The multi-camera endoscope may further include a pathway fluid injector for inflating and/or cleaning a body cavity into which the endoscope is inserted.

There is provided, according to some embodiments, a tip section of a multi-camera endoscope, the tip section comprising: two or more side-pointing cameras positioned at or in proximity to a distal end of the tip section, wherein each of the two or more side-pointing cameras having a discrete illuminator associated therewith, wherein the field of view provided by the two or more side-pointing cameras covers a front and side views; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein the tip section comprises: two or more side-pointing cameras positioned at or in proximity to a distal end of the tip section, wherein each of the two or more side-pointing cameras having a discrete illuminator associated therewith, wherein the field of view provided by the two or more side-pointing cameras covers a front and side views; a working channel configured for insertion of a surgical tool; and a pathway fluid injector for inflating and/or cleaning a body cavity into which the endoscope is inserted.

The tip section may further include two or more side fluid injectors configured for cleaning the two or more side-pointing cameras and/or the discrete side illuminators. The two or more side-pointing cameras may point at directions essentially opposing to one another. The tip section may include three or more side-pointing cameras. According to some embodiments, the three or more side-pointing cameras may be positioned essentially at equal distances from each other along the perimeter of the tip section.

There is provided, according to some embodiments, a tip section of a multi-camera endoscope, the tip section comprising: a front-pointing camera and a discrete front illuminator associated therewith; a front fluid injector configured for cleaning at least one of the front-pointing camera and the discrete front illuminator; a side-pointing camera; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein the tip section comprises: two or more side-pointing cameras positioned at or in proximity to a distal end of the tip section, wherein each of the two or more side-pointing cameras having a discrete illuminator associated therewith, wherein the field of view provided by the two or more side-pointing cameras covers a front and side views; a working channel configured for insertion of a surgical tool; and a pathway fluid injector for inflating and/or cleaning a body cavity into which the endoscope is inserted. The tip section may further include a discrete side illuminator associated with side-pointing camera. The tip section may further include a side fluid injector configured for cleaning the side-pointing camera and/or the discrete side illuminator.

There is provided, according to an embodiment, a multi-camera endoscope comprising: an elongated shaft terminating with a tip section turnable by way of a bending section, wherein the tip section comprises: a front-pointing camera and a discrete front illuminator associated therewith; a front fluid injector configured for cleaning at least one of the front-pointing camera and the discrete front illuminator; a side-pointing camera and a discrete side illuminator associated therewith; a side fluid injector configured for cleaning at least one of the side-pointing camera and the discrete side illuminator; a working channel configured for insertion of a surgical tool; and a pathway fluid injector for inflating and/or cleaning a body cavity into which the endoscope is inserted.

There is further provided, according to an embodiment, a multi-camera endoscopy system comprising: an endoscope comprising a handle and an elongated shaft terminating with a tip section turnable by way of a bending section, wherein the tip section comprises: a front-pointing camera and a discrete front illuminator associated therewith, a front fluid injector configured for cleaning at least one of the front-pointing camera and the discrete front illuminator, a side-pointing camera and a discrete side illuminator associated therewith, a side fluid injector configured for cleaning at least one of the side-pointing camera and the discrete side illuminator, a working channel configured for insertion of a surgical tool, and a pathway fluid injector for inflating and/or cleaning a body cavity into which the endoscope is inserted; a controller connected to the handle of the endoscope by way of a utility cable; and a display connected to the controller and configured to display video streams received from the front and side-pointing cameras.

In some embodiments, the front-pointing camera and the side-pointing camera are pointing at directions essentially perpendicular to one another.

In some embodiments, the front-pointing camera and the side-pointing camera are pointing approximately 100 to 145 degrees relative to one another.

In some embodiments, a center of the side-pointing camera is positioned approximately 7 to 11 millimeters from a distal end of the tip section.

In some embodiments, each of the discrete front and side illuminators comprises a light-emitting diode (LED).

In some embodiments, at least one of the discrete front and side illuminators is configured to emit white light.

In some embodiments, at least one of the discrete front and side illuminators is configured to emit ultraviolet light.

In some embodiments, at least one of the discrete front and side illuminators is configured to emit infrared light.

In some embodiments, at least one of the discrete front and side illuminators is configured to emit near-infrared light.

In some embodiments, the discrete front and side illuminators are configured to emit light in different wavelengths.

In some embodiments, the tip section further comprises an additional discrete front illuminator configured to emit light having a different wavelength than the discrete front illuminator.

In some embodiments, the additional discrete front illuminator and the discrete front illuminator are configured to simultaneously emit light, each at a different wavelength.

In some embodiments, the tip section further comprises an additional discrete side illuminator configured to emit light having a different wavelength than the discrete side illuminator.

In some embodiments, the additional discrete side illuminator and the discrete side illuminator are configured to simultaneously emit light, each at a different wavelength.

In some embodiments, each of the front-pointing camera and the side-pointing camera comprises a Charge Coupled Device (CCD) or a Complementary Metal Oxide Semiconductor (CMOS) image sensor.

In some embodiments, the front and side fluid injectors are connected to a same fluid supply channel.

In some embodiments, the pathway fluid injector is connected to the fluid supply channel, together with the front and side fluid injectors.

In some embodiments, at least one of the front and side-pointing cameras comprises a lens assembly providing a field of view of 90 degrees or more.

In some embodiments, at least one of the front and side-pointing cameras comprises a lens assembly providing a field of view of 120 degrees or more.

In some embodiments, at least one of the front and side-pointing cameras comprises a lens assembly providing a field of view of 150 degrees or more.

In some embodiments, the front-pointing camera comprises a lens assembly providing a focal length of approximately 3-100 millimeters.

In some embodiments, the side-pointing camera comprises a lens assembly providing a focal length of approximately 2-33 millimeters.

In some embodiments, the tip section further comprises an opposite side-pointing camera pointing at a direction essentially opposite to the side-pointing camera.

In some embodiments, the tip section further comprises a perpendicular side-pointing camera pointing at a direction essentially perpendicular to the side-pointing camera.

In some embodiments, the endoscope is a colonoscope.

In some embodiments, fields of view of the front-pointing camera and side-pointing camera are at least partially overlapping, such that an object of interest viewed via the side-pointing camera remains in the field of view of the side-pointing camera while the tip section is being turned towards the object, and at least until the object becomes visible through the front-pointing camera.

In some embodiments, the utility cable comprises: a fluid channel for providing a fluid to at least one of the injectors; a data cable for receiving video signals from the front and side-pointing cameras; and a power cable for providing electrical power to the front and side-pointing cameras and to the discrete front and side illuminators.

In some embodiments, the controller is configured to process and combine video signals received from the front and side-pointing cameras into a single panoramic video view.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

An aspect of some embodiments relates to an endoscope having a tip section equipped with two or more cameras. According to one embodiment, one of the cameras is positioned at a distal end of the tip section and points forward, and the remaining camera(s) is positioned further back in the tip section, and points sideways.

According to another embodiment, one of the cameras is positioned at a distal (front) end surface of the tip section and points forward, and the remaining camera(s) is positioned further back in the tip section, and points sideways.

According to another embodiment, two or more cameras (for example, three, four or more) are positioned in proximity to or at the distal end of the tip section and point sideways such that the field of view provided by the cameras covers a front and side views. Even though in such configuration, according to some embodiments, no camera is positioned at the distal (front) end surface of the tip section (or in other words, no camera is pointing directly forward), still the field of view of the side cameras allows view of the front direction of the tip and accordingly of the endoscope.

This configuration, advantageously, may allow for a higher rate of detection, compared to conventional configurations, of pathological objects that exist in the body cavity in which the endoscope operates.

The cameras and optionally other elements that exist in the tip section (such as a light source, a working channel, a fluid injector and/or the like) are uniquely scaled, configured and packaged so that they fit within the minimalistic space available inside the tip section, while still providing valuable results.

Figure 1:
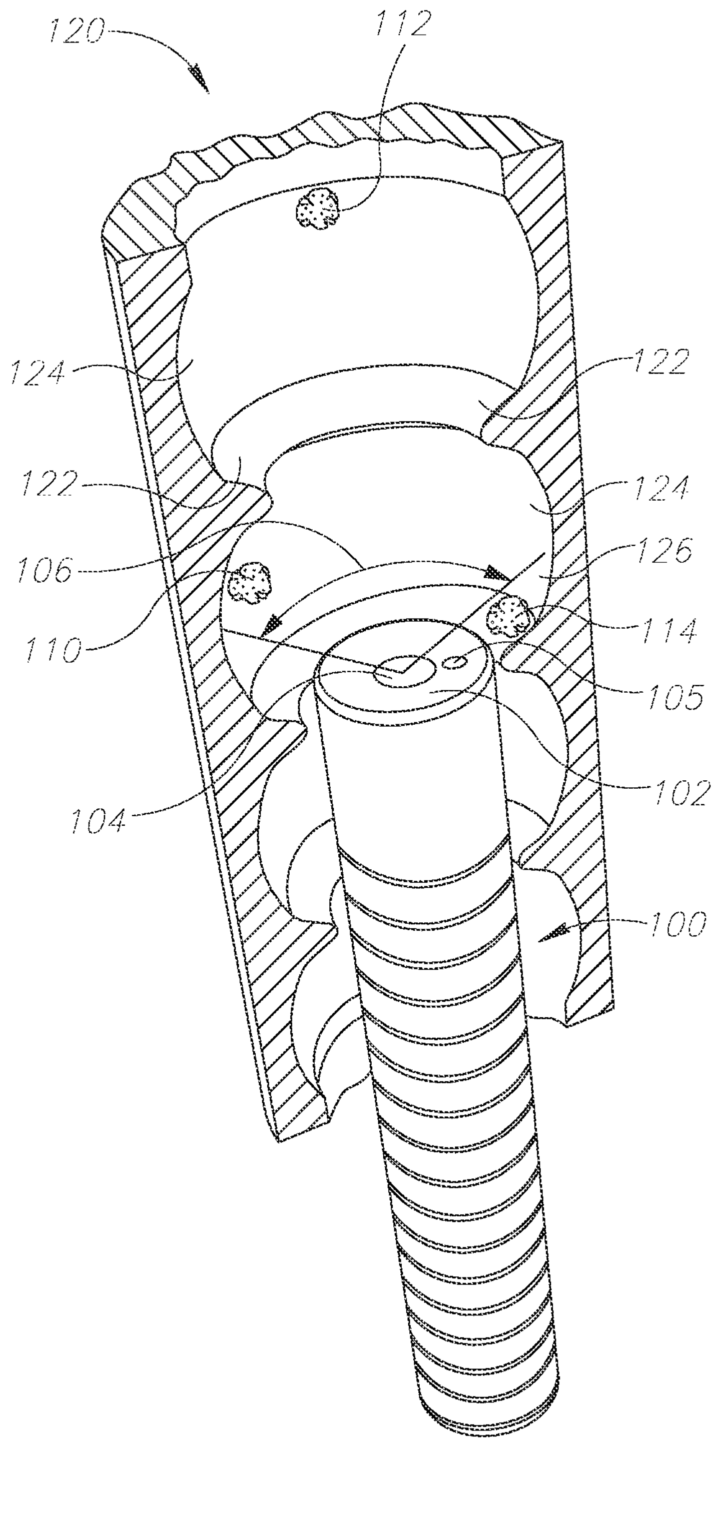
FIG. 1 shows a cross sectional view of a prior art endoscope.

Reference is now made to FIG. 1, which shows a cross sectional view of a prior art endoscope, in this example a colonoscope 100, used within a colon 120 of a patient. The human colon includes a series of annular muscles which appear in this figure as folds 122 protruding from an inner surface 124 of the colon.

Endoscope 100 includes a front-pointing camera 104 positioned at a distal end 102 of the colonoscope. Camera 104 typically has a wide field of view 106. When endoscope 100 is used within a body cavity such as colon 120, the operator advances the endoscope 100 while viewing images (commonly a video feed) transmitted by camera 104. When a polyp, such as polyp 110 or 112 is discovered on a wall of colon 120, the operator may insert a surgical tool (not shown) through a working channel 105 to remove, treat and/or extract a sample of the polyp or its entirety for biopsy.

However, in some cases, a polyp, such as polyp 114 may be located on an inner side of a fold 126, such that it is hidden from the field of view 106 of camera 104. This phenomena greatly contributes to the common statistics, according to which as many as 12-24% of polyps are missed during colonoscopy. Missing polyps, or a "false negative" diagnosis, may result in late discovery of cancer.

Figure 2:
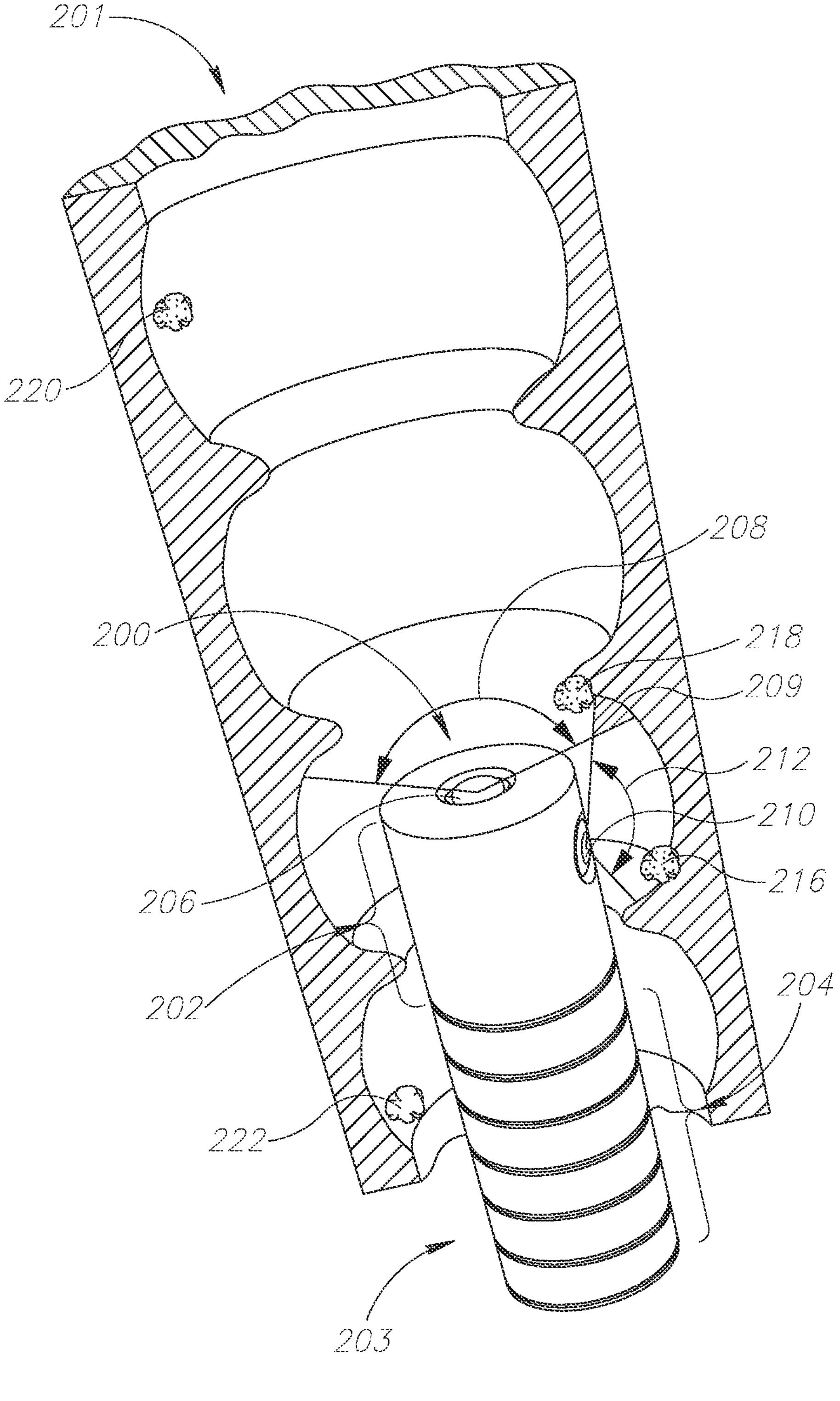
FIG. 2 shows a cross section of a multi-camera endoscope, according to some embodiments.

Reference is now made to FIG. 2, which shows a cross section of a multi-camera endoscope 200, according to an embodiment. Endoscope 200 may include an elongated shaft 203 (not fully shown) terminating with a tip section 202 which is turnable by way of a bending section 204. Advantageously, tip section may include a front-pointing camera 206 as well as a side-pointing camera 210. While front-pointing camera 206 may be able to detect, based on its field of view 208, polyps such as polyps 218 and 220, side-pointing camera 210 may be further able to detect polyps which are normally hidden from the front-pointing camera, such as polyp 216. By rotating endoscope 200 around its longitude, side-pointing camera 210 may detect polyps circumferentially, 360 degrees around the endoscope. This may enable the detection of polyps such as a polyp 222, which is, similar to polyp 216, located on an inner side of a fold. In other configurations (not shown), two or more side-pointing cameras may exist in the tip section, each having a different (or an overlapping, to some degree) field of view.

Advantageously, the fields of view of front-pointing camera 206 and side-pointing camera 210 are at least partially overlapping, such that an object of interest (such as a polyp or another pathology) viewed via the side-pointing camera remains in the field of view of this camera while the tip section is being turned towards the object, and at least until the object becomes visible through the front-pointing camera. This may be beneficial when a polyp is discovered by side-pointing camera 210, and the operator desires to perform a surgical operation on that polyp using a surgical tool inserted through a working channel (not shown in the figure) which has an opening in a distal end surface of tip section 202, next to front-pointing camera 206. For performing the surgical operation, tip section 202 may need to be turned towards the polyp. It may greatly assist the operator if the fields of view of front-pointing camera 206 and side-pointing camera 210 have some overlap, so that the polyp remains in sight throughout the turning of the tip section and the operator does not get disoriented.

Figure 3:
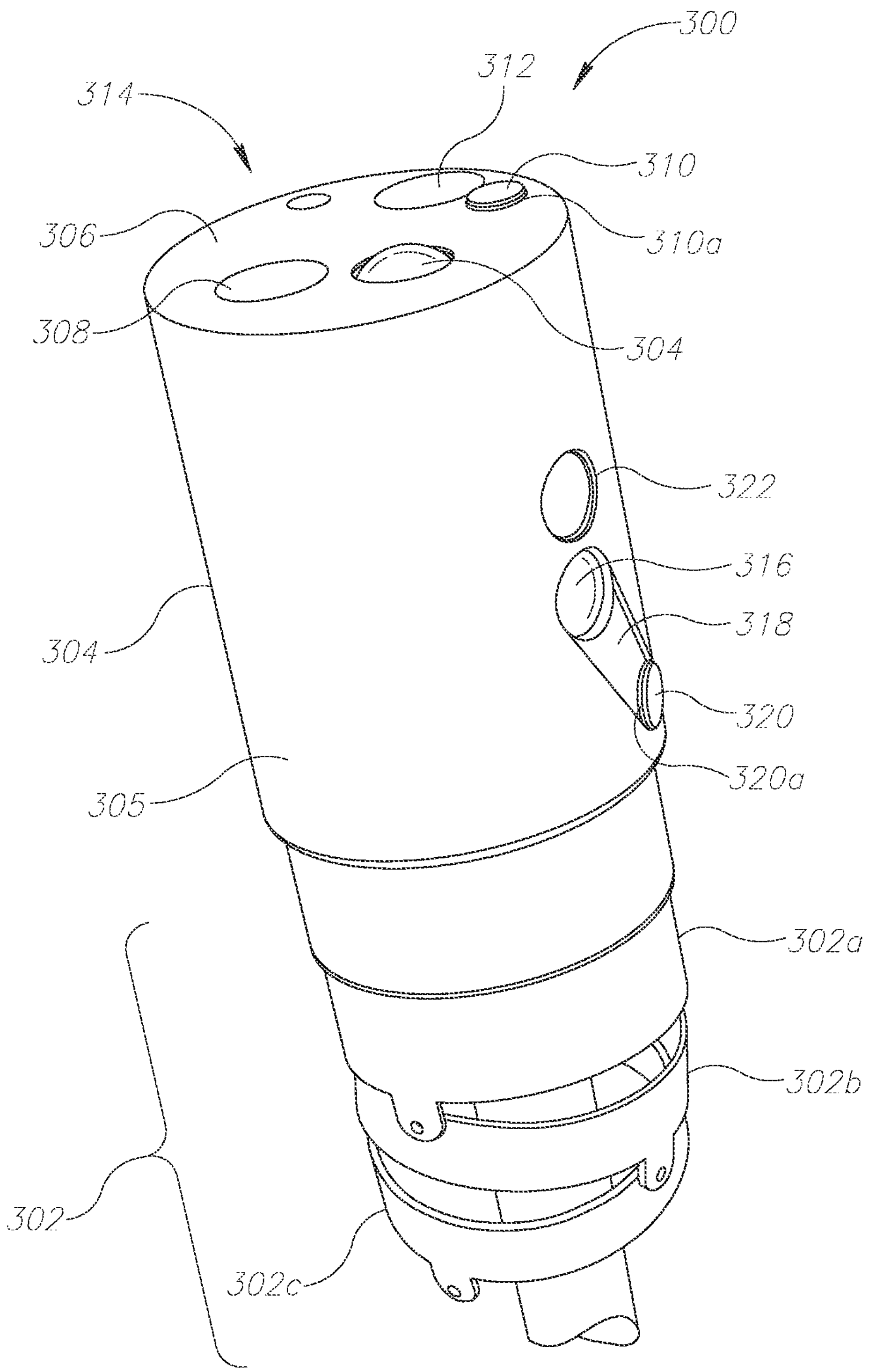
FIG. 3 shows a perspective view of a multi-camera endoscope, according to some embodiments.

Reference is now made to FIG. 3, which shows a perspective view of a multi-camera endoscope 300 in more detail, according to an embodiment. Endoscope 300 may include an elongated shaft (not shown), a bending section (partially shown) 302 and a tip section 304 which terminates the endoscope.

Bending section 302 may include a plurality of links, such as links 302*a-c*, which enable the turning of tip section 304 in different directions. In a different configuration (not shown), a bending section may be constructed differently, as long as it enables the turning of the tip section in different directions. Bending section 302 may be covered with an elastic sheath (not shown), which may also extend to cover the elongated shaft.

Tip section 304 may include therein a front-pointing camera 304 which may capture images through a hole in a distal end surface 306 of the tip section. A discrete front illuminator 308, which is optionally a light-emitting diode (LED), may be associated with front-pointing camera 304 and used for illuminating its field of view through another hole in distal end surface 306. The LED may be a while light LED, an infrared light LED, a near infrared light LED or an ultraviolet light LED. The term "discrete", in regard to front illuminator 308, may refer to an illumination source which generates light internally—in contrast to a non-discrete illuminator which may be, for example, a fiber optic merely transmitting light generated remotely. In a different configuration (not shown), two or more discrete front illuminators may be present in the tip section, such as for supplying overall stronger illumination and/or for increasing the angular coverage of the illumination. These two or more discrete front illuminators may be located next to one another so that they share a same protective window on the distal end surface of the tip section.

A front fluid injector 310 may be used for cleaning at least one of front-pointing camera 304 and discrete front illuminator 308. Front fluid injector 310 may be slightly elevated from distal end surface 306, to enable it to inject fluid, from its side 310*a*, onto front-pointing camera 304 and discrete front illuminator 308. Front fluid injector 310 may be configured to inject fluids such as water, air and/or the like.

Distal end surface 306 may further include a hole defining a working channel 312. Working channel 312 may be a hollow tube configured for insertion of a surgical tool to operate on various tissues. For example, miniature forceps may be inserted through working channel 312 in order to remove a polyp or sample of which for biopsy.

A pathway fluid injector 314, defined by another hole in distal end surface 306, may be used for inflating and/or cleaning the body cavity into which endoscope 300 is inserted. Inflation may be performed by flowing air or another gas through pathway fluid injector 314, and may be beneficial for cases in which the body cavity, such as the colon, is shriveled or otherwise does not allow for efficient inspection. Cleaning may be achieved, for example, by injecting a liquid, such as water or saline, on an unclean area of the body cavity. Furthermore, pathway fluid injector 314 (or a different tube, not shown) may be used for applying suction, in order to evacuate various liquids and/or solids which exist in the body cavity and interfere with the inspection.

Tip section 304 may further include therein a side-pointing camera 316 which may capture images through a hole in a cylindrical surface 305 of the tip section. A discrete side illuminator 322, which is optionally similar to discrete front illuminator 308, may be associated with front-pointing camera 304 and used for illuminating its field of view through another hole in cylindrical surface 305. In a different configuration (not shown), two or more discrete side illuminators may be present in the tip section, such as for supplying overall stronger illumination and/or for increasing the angular coverage of the illumination. These two or more discrete side illuminators may be located next to one another so that they share a same protective window on the cylindrical surface of the tip section.

A side fluid injector 320 may be used for cleaning at least one of side-pointing camera 304 and discrete side illuminator 322. In order to prevent tissue damage when cylindrical surface 305 of tip section 304 contacts a side wall of the body cavity, side fluid injector 320 and side-pointing camera 316 may be located in a depression 318 in the cylindrical surface. This way, side fluid injector 320 may be elevated from depression 318 but still not significantly protrude from the level of cylindrical surface 305. The elevation of side fluid injector 320 may enable it to inject fluid, from its side 320*a*, onto side-pointing camera 316. In an alternative configuration (not shown), one or more discrete side illuminators may also be included in the depression, so that fluid injected from the side fluid injector may reach them. In yet another configuration (not shown), a side-pointing camera, one or more side illuminators and a side fluid injector may not be located in a depression, but rather be on essentially the same level as the cylindrical surface of the tip section.

Figure 4:
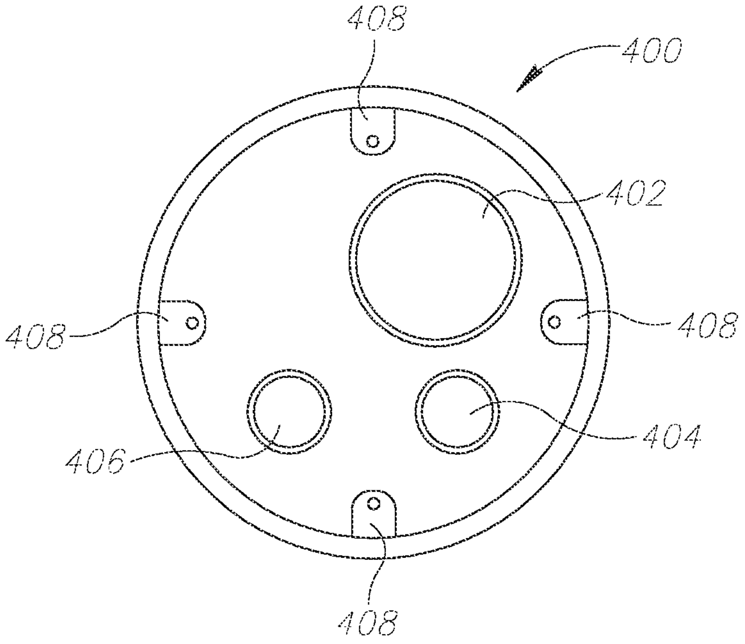
FIG. 4 shows a cross-sectional view of a bending section of a multi-camera endoscope, according to some embodiments.

Reference is now made to FIG. 4, which shows a cross-sectional view of a bending section 400 of a multi-camera endoscope, such as multi-camera endoscope 300 of FIG. 3. A plurality of steering cable eyes, such as four eyes 408, are positioned on the internal walls of bending section 400. Through these eyes 408, steering cables are threaded, to enable the maneuvering of bending section 400. Bending section 400 may also include a working channel 402, through which surgical tools may be inserted, a fluid channel 406, through which fluids and/or liquids may be infused, and an electrical channel 404, through which a plurality of electrical cables may be threaded, for transmitting video signals from the cameras and for supplying power to the cameras and the discrete illuminators.

For simplicity of presentation, FIG. 4 only shows a single working channel 402, although in a different configuration (not shown), more than one working channel may exist, to enable the insertion of multiple surgical tools simultaneously. Similarly, only one fluid channel 406 is shown, although in a different configuration (not shown) more than one fluid channel may be used, such as for separately feeding at least one of a front fluid injector, a side fluid injector and/or a pathway fluid injector, as well as for separately providing suction through the pathway fluid injector. Additionally, FIG. 4 shows only a single electrical channel 404, but in other configurations (not shown), one or more of the electrical cables threaded through the elongated shaft and/or the bending section may be separated into a plurality of tubes, for example in order to distance cables causing magnetic induction from cables which may be influenced by this phenomena.

Figure 5A:
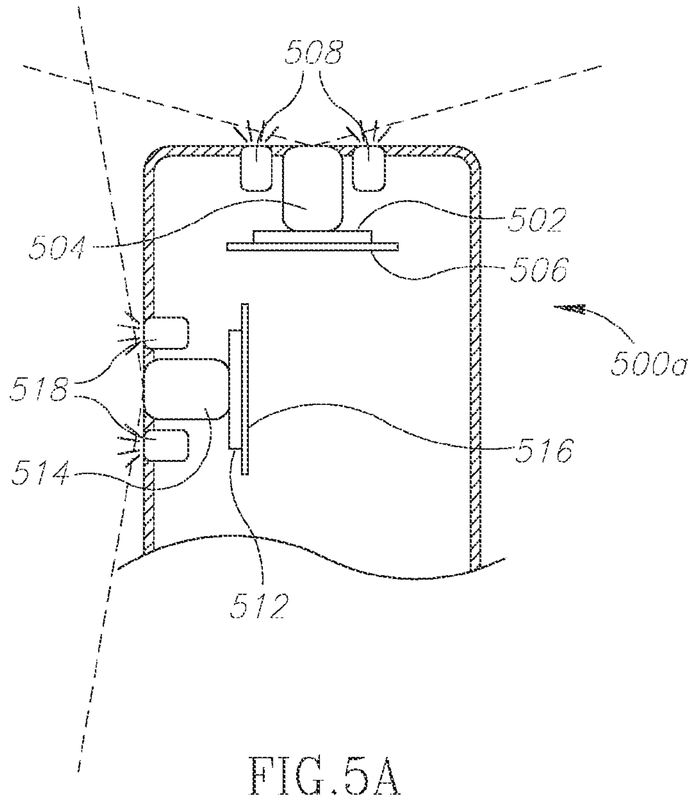
FIGS. 5 A-B show a cross-sectional views of tip sections of multi-camera endoscopes, according to some embodiments.

Reference is now made to FIG. 5A, which shows a cross-sectional view of a tip section 500*a* of a multi-camera endoscope, according to an embodiment. Tip section 500*a* may include a front-pointing image sensor 502, such as Charge Coupled Device (CCD) or a Complementary Metal Oxide Semiconductor (CMOS) image sensor. Front-pointing image sensor 502 may be mounted on an integrated circuit board 506, which may be rigid or flexible. Integrated circuit board 506 may supply front-pointing image sensor 502 with the necessary electrical power, and may derive still images and/or video feeds captured by the image sensor. Integrated circuit board 506 may be connected to a set of electrical cables (not shown) which may be threaded through an electrical channel running through the elongated shaft of the endoscope. Front-pointing image sensor 502 may have a lens assembly 504 mounted on top of it and providing the necessary optics for receiving images. Lens assembly 504 may include a plurality of lenses, static or movable, which may provide a field of view of at least 90 degrees and up to essentially 180 degrees. Lens assembly 504 may provide a focal length of about 3 to 100 millimeters. Front-pointing image sensor 502 and lens assembly 504, with or without integrated circuit board 506, may be jointly referred to as a "front pointing camera".

One or more discrete front illuminators 508 may be placed next to lens assembly 504, for illuminating its field of view. Optionally, discrete front illuminators 508 may be attached to the same integrated circuit board 506 on which front-pointing image sensor 502 is mounted (this configuration is not shown).

Tip section 500*a* may include a side-pointing image sensor 512, such as Charge Coupled Device (CCD) or a Complementary Metal Oxide Semiconductor (CMOS) image sensor. Front-pointing image sensor 512 may be mounted on an integrated circuit board 516, which may be rigid or flexible. Integrated circuit board 516 may supply side-pointing image sensor 512 with the necessary electrical power, and may derive still images and/or video feeds captured by the image sensor. Integrated circuit board 516 may be connected to a set of electrical cables (not shown) which may be threaded through an electrical channel running through the elongated shaft of the endoscope.

Side-pointing image sensor 512 may have a lens assembly 514 mounted on top of it and providing the necessary optics for receiving images. Lens assembly 514 may include a plurality of lenses, static or movable, which may provide a field of view of at least 90 degrees and up to essentially 180 degrees. Lens assembly 514 may provide a focal length of about 2 to 33 millimeters. Side-pointing image sensor 512 and lens assembly 514, with or without integrated circuit board 516, may be jointly referred to as a "side pointing camera".

One or more discrete side illuminators 518 may be placed next to lens assembly 514, for illuminating its field of view. Optionally, discrete side illuminators 518 may be attached to the same integrated circuit board 516 on which side-pointing image sensor 512 is mounted (this configuration is not shown).

In another configuration (not shown), integrated circuit boards 506 and 516 may be a single integrated circuit board on which both front and side-pointing image sensors 502 and 512 are mounted. For this purpose, the integrated circuit board may be essentially L-shaped.

Front and side-pointing image sensors 502 and 512 may be similar or identical in terms of, for example, field of view, resolution, light sensitivity, pixel size, focal length, focal distance and/or the like.

Optionally, side-pointing image sensor 512 and lens assembly 514 are advantageously positioned relatively close to the distal end surface of tip section 500*a*. For example, a center of the side-pointing camera (which is the center axis of side-pointing image sensor 512 and lens assembly 514) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

Figure 5B:
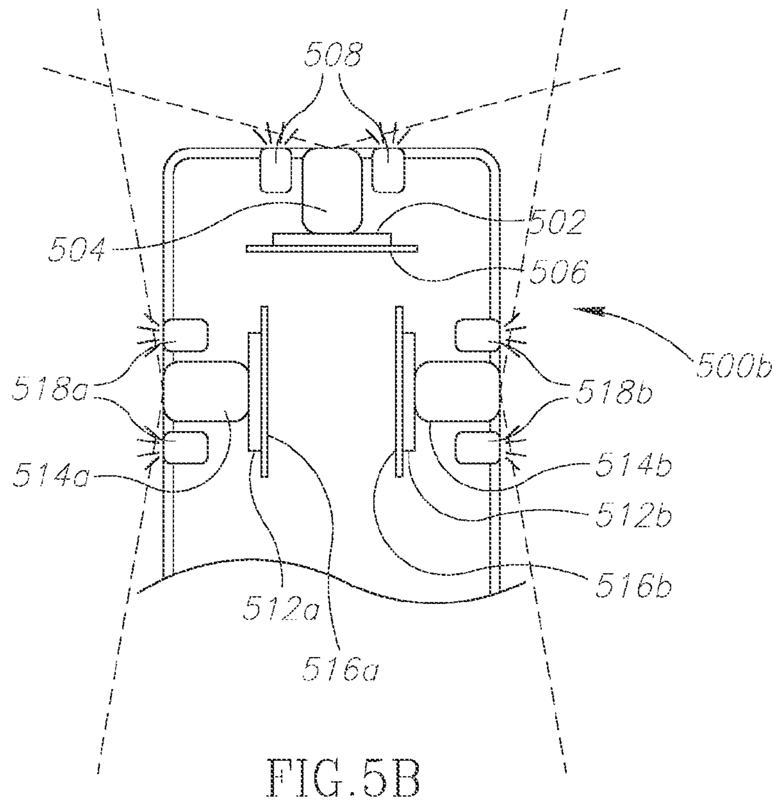

Reference is now made to FIG. 5B, which shows a cross-sectional view of a tip section 500*b* of a multi-camera endoscope, according to another embodiment of the invention. Tip section 500*b*, similar to tip section 500*a* of FIG. 5A, may include a front-pointing image sensor 502, such as Charge Coupled Device (CCD) or a Complementary Metal Oxide Semiconductor (CMOS) image sensor. Front-pointing image sensor 502 may be mounted on an integrated circuit board 506, which may be rigid or flexible. Integrated circuit board 506 may supply front-pointing image sensor 502 with the necessary electrical power, and may derive still images and/or video feeds captured by the image sensor. Integrated circuit board 506 may be connected to a set of electrical cables (not shown) which may be threaded through an electrical channel running through the elongated shaft of the endoscope. Front-pointing image sensor 502 may have a lens assembly 504 mounted on top of it and providing the necessary optics for receiving images. Lens assembly 504 may include a plurality of lenses, static or movable, which may provide a field of view of at least 90 degrees and up to essentially 180 degrees. Lens assembly 504 may provide a focal length of about 3 to 100 millimeters. Front-pointing image sensor 502 and lens assembly 504, with or without integrated circuit board 506, may be jointly referred to as a "front pointing camera". One or more discrete front illuminators 508 may be placed next to lens assembly 504, for illuminating its field of view. Optionally, discrete front illuminators 508 may be attached to the same integrated circuit board 506 on which front-pointing image sensor 502 is mounted (this configuration is not shown).

Tip section 500*b* may include, in addition to side-pointing image sensor 512*a*, another side-pointing image sensor 512*b*. Side-pointing image sensors 512*a* and 512*b* may include Charge Coupled Device (CCD) or a Complementary Metal Oxide Semiconductor (CMOS) image sensor. Side-pointing image sensors 512*a* and 512*b* may be mounted on integrated circuit boards 516*a* and 516*b*, respectively, which may be rigid or flexible. Integrated circuit boards 516*a* and 516*b* may supply side-pointing image sensors 512*a* and 512*b* with the necessary electrical power, and may derive still images and/or video feeds captured by the image sensor. Integrated circuit boards 516*a* and 516*b* may be connected to a set of electrical cables (not shown) which may be threaded through an electrical channel running through the elongated shaft of the endoscope.

Side-pointing image sensors 512*a* and 512*b* may have lens assemblies 514*a* and 514*b*, respectively, mounted on top of them and providing the necessary optics for receiving images. Lens assemblies 514*a* and 514*b* may include a plurality of lenses, static or movable, which may provide a field of view of at least 90 degrees and up to essentially 180 degrees. Lens assemblies 514*a* and 514*b* may provide a focal length of about 2 to 33 millimeters. Side-pointing image sensors 512*a* and 512*b* and lens assemblies 514*a* and 514*b*, with or without integrated circuit boards 516*a* and 516*b*, respectively, may be jointly referred to as a "side pointing cameras".

Discrete side illuminators 518*a* and 518*b* may be placed next to lens assemblies 514*a* and 514*b*, respectively, for illuminating its field of view. Optionally, discrete side illuminators 518*a* and 518*b* may be attached to the same integrated circuit boards 516*a* and 516*b* on which side-pointing image sensors 512*a* and 512*b* are mounted (this configuration is not shown).

In another configuration (not shown), integrated circuit boards 506, 516*a* and 516*b* may be a single integrated circuit board on which front and side-pointing image sensors 502, 512*a* and 512*b* are mounted.

Front and side-pointing image sensors 502, 512*a* and 512*b* may be similar, identical or distinct in terms of, for example, field of view, resolution, light sensitivity, pixel size, focal length, focal distance and/or the like.

Optionally, side-pointing image sensors 512*a* and 512*b* and lens assemblies 514*a* and 514*b* are advantageously positioned relatively close to the distal end surface of tip section 500*b*. For example, a center of the side-pointing cameras (which is the center axis of side-pointing image sensors 512*a* and 512*b* and lens assemblies 514*a* and 514*b*) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

According to some embodiments, the front and side-pointing cameras are all positioned on the same (imaginary) plain which "divides" tip section 500*b* into two equal parts along its length. According to some embodiments, each of the side-pointing cameras is perpendicular to the front pointing camera.

Figure 6:
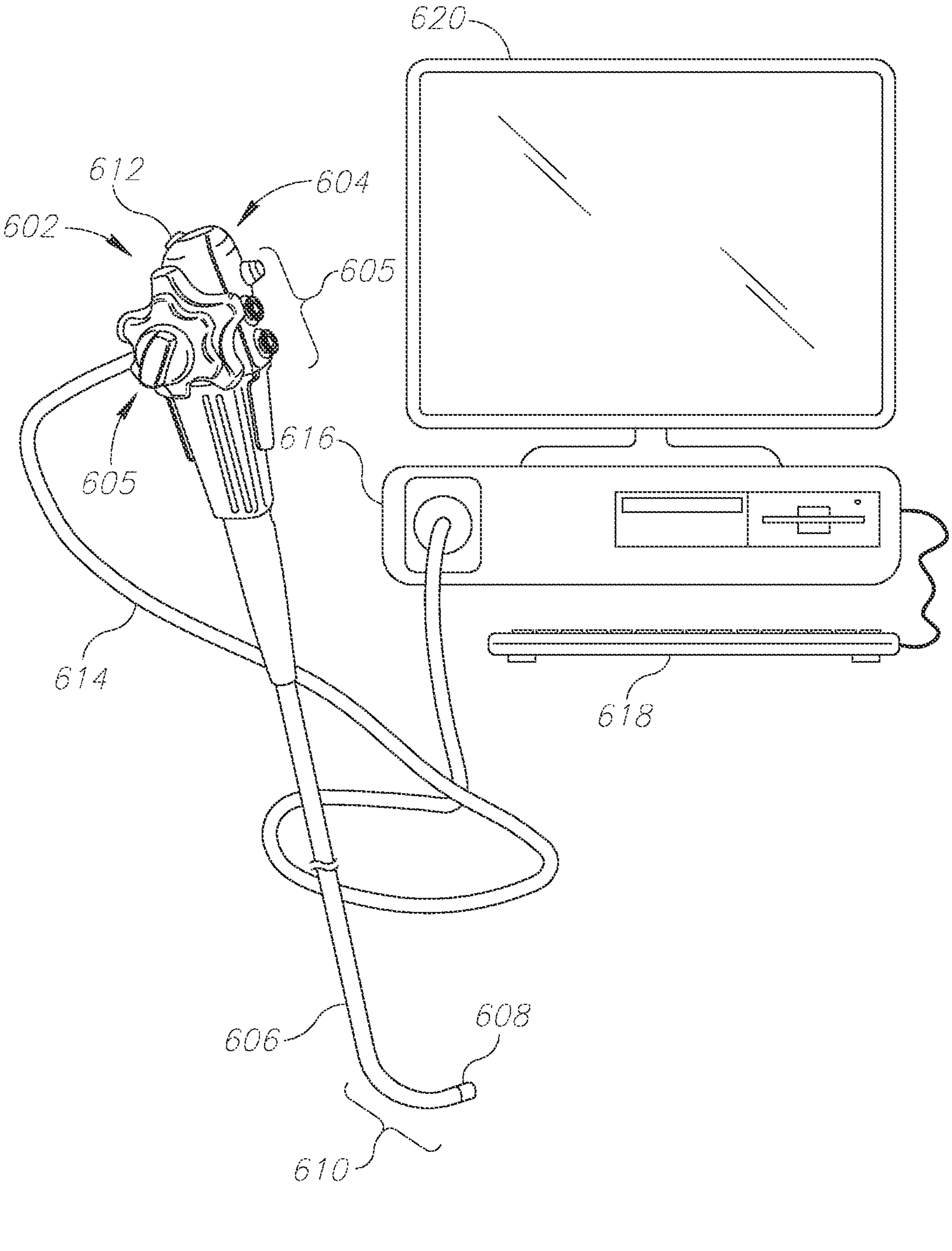
FIG. 6 shows a semi-pictorial view of a multi-camera endoscopy system, according to some embodiments.
Figure 7A:
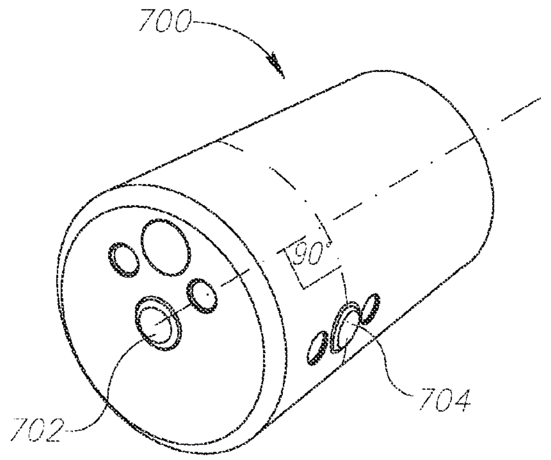
FIGS. 7A-D show perspective views of multiple tip section configurations, according to some embodiments.
Figure 7B:
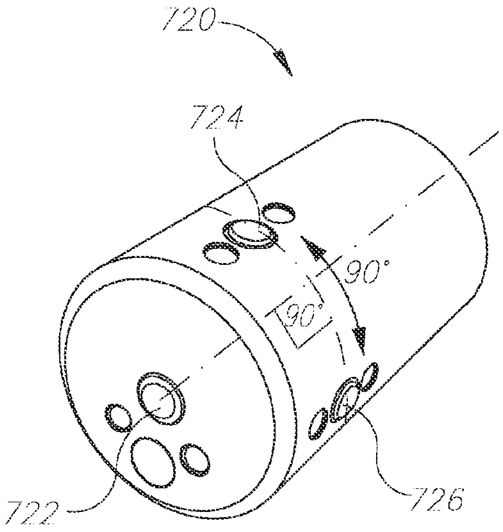
Figure 7C:
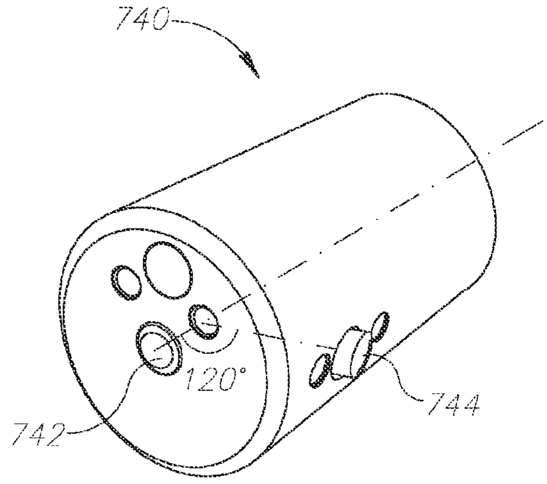
Figure 7D:
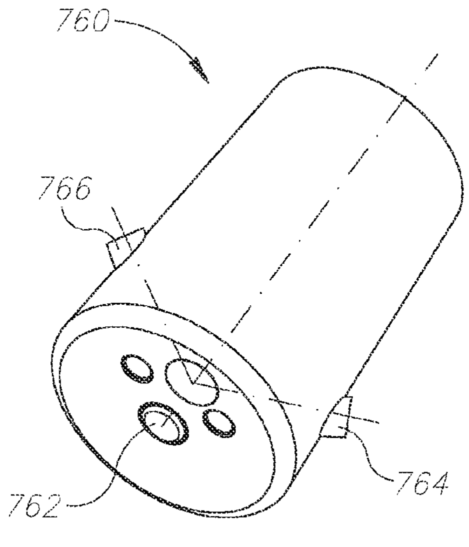

Reference is now made to FIG. 6, which shows a semi-pictorial view multi-camera endoscopy system 600. System 600 may include a multi-camera endoscope 602, such as the endoscope of FIGS. 2, 3, 4 and/or 5. Multi-camera endoscope 602 may include a handle 604, from which an elongated shaft 606 emerges. Elongated shaft 606 terminates with a tip section 608 which is turnable by way of a bending section 610. Handle 604 may be used for maneuvering elongated shaft 606 within a body cavity; the handle may include one or more knobs and/or switches 605 which control bending section 610 as well as functions such as fluid injection and suction. Handle 604 may further include a working channel opening 612 through which surgical tools may be inserted.

A utility cable 614 may connect between handle 604 and a controller 616. Utility cable 614 may include therein one or more fluid channels and one or more electrical channels. The electrical channel(s) may include at least one data cable for receiving video signals from the front and side-pointing cameras, as well as at least one power cable for providing electrical power to the cameras and to the discrete illuminators.

Controller 616 may govern power transmission to the endoscope's 602 tip section 608, such as for the tip section's cameras and illuminators. Controller 616 may further control one or more fluid, liquid and/or suction pump which supply corresponding functionalities to endoscope 602. One or more input devices, such as a keyboard 618, may be connected to controller 616 for the purpose of human interaction with the controller. In another configuration (not shown), an input device, such as a keyboard, may be integrated with the controller in a same casing.

A display 620 may be connected to controller 616, and configured to display images and/or video streams received from the cameras of multi-camera endoscope 602. Display 620 may further be operative to display a user interface for allowing a human operator to set various features of system 600.

Optionally, the video streams received from the different cameras of multi-camera endoscope 602 may be displayed separately on display 620, either side-by-side or interchangeably (namely, the operator may switch between views from the different cameras manually). Alternatively, these video streams may be processed by controller 616 to combine them into a single, panoramic video frame, based on an overlap between fields of view of the cameras.

In another configuration (not shown), two or more displays may be connected to controller 616, each for displaying a video stream from a different camera of the multi-camera endoscope.

Reference is now made to FIGS. 7A-D, in which multiple configurations 700, 720, 740 and 760 of a tip section are shown.

In configuration 700, a front-pointing camera 702 and a side-pointing camera 704 are essentially perpendicular to one another, and have, correspondingly, perpendicular fields of view.

In configuration 720, a front-pointing camera 722 is essentially perpendicular to a first side-pointing camera 724 and a second side-pointing camera 726. First and second side-pointing cameras 724-726 are pointing perpendicularly to one another, and are positioned essentially 90 degrees apart in the cylindrical surface of the tip section. In another configuration (not shown), a first and a second side-pointing cameras may be positioned more than 90 degrees apart in the cylindrical surface of the tip section, such as 120-150 degrees apart or 150-180 degrees apart. For example, the first and second side-pointing cameras may be positioned in 180 degrees apart, in opposite sides of the cylindrical surface of the tip section, so that they point in opposite directions. In yet further configurations (not shown), three or more side-pointing cameras may be positioned in the cylindrical surface of the tip section, for example, three cameras having 120 degrees in between them.

In configuration 740, a side-pointing camera 744 is pointing slightly backwards, so that it forms an angle larger than 90 degrees relative to a front-pointing camera 742. As an example, an angle of 120 degrees is shown. In another configuration (not shown), the angle is 100-145 degrees.

In configuration 760, two opposing side cameras, 764 and 766, are shown, which are pointing slightly backwards, so that they each form an angle larger than 90 degrees relative to a front-pointing camera 762. As an example, an angle of 120 degrees is shown. In another configuration (not shown), the angle is 100-145 degrees.

Similarly, in other configurations (not shown), three or more side-pointing cameras may be positioned in the cylindrical surface of the tip section, each pointing slightly backwards and having an certain angle in between; in the case of three cameras, they may have an angle of 120 degrees in between them.

Figure 8:
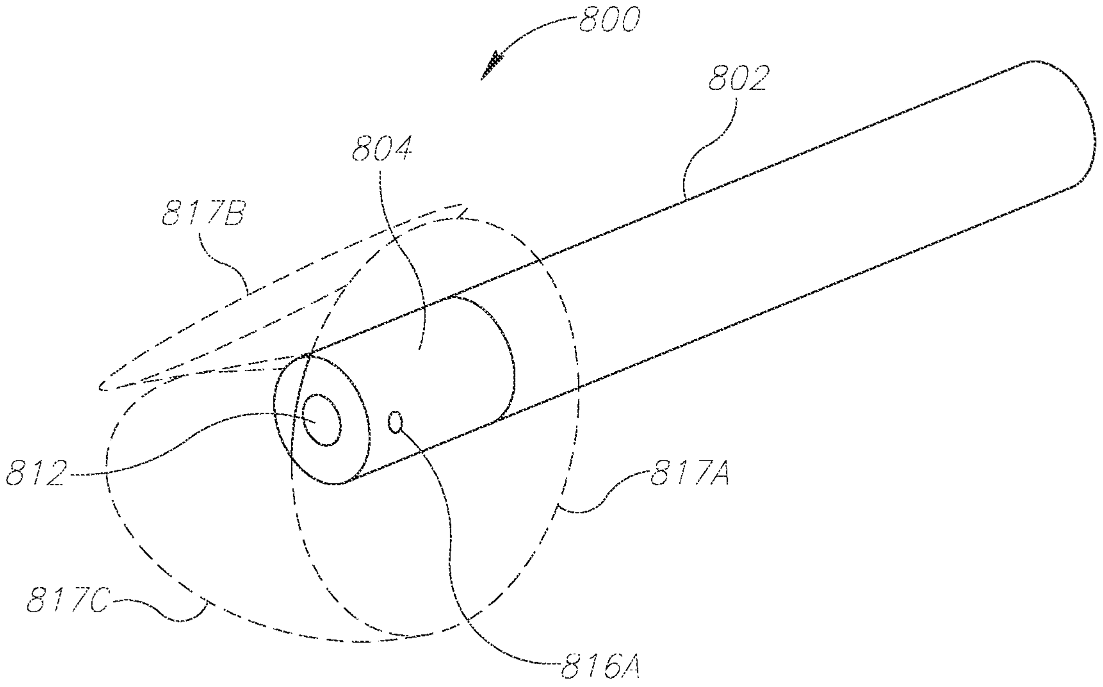
FIG. 8 shows a perspective view of a multi-camera endoscope, according to some embodiments.

Reference is now made to FIG. 8, which shows a perspective view of a multi-camera endoscope, according to some embodiments. Endoscope 800 includes an elongated shaft 802 which typically includes a bending section (not shown) and a tip section 804 which terminates the endoscope. Tip section 804 includes three side-pointing cameras 816*a*, 816*b* (not shown) and 816*c* (not shown). Discrete side illuminators (for example LEDs), not shown, may be associated with the side-pointing cameras 816*a-c* for illuminating their respective fields of view 817*a-c*. Tip section 804 includes further includes a working channel 812 which may be a hollow opening configured for insertion of a surgical tool to operate on various tissues. For example, miniature forceps may be inserted through working channel 812 in order to remove a polyp or sample of which for biopsy.

Tip 804 may further include other elements/components, (for example, as described herein according to various embodiments) such as fluid injector(s) for cleaning the cameras and/or there illuminators and pathway fluid injector(s) for inflating and/or cleaning the body cavity into which endoscope 800 is inserted.

Figure 9:
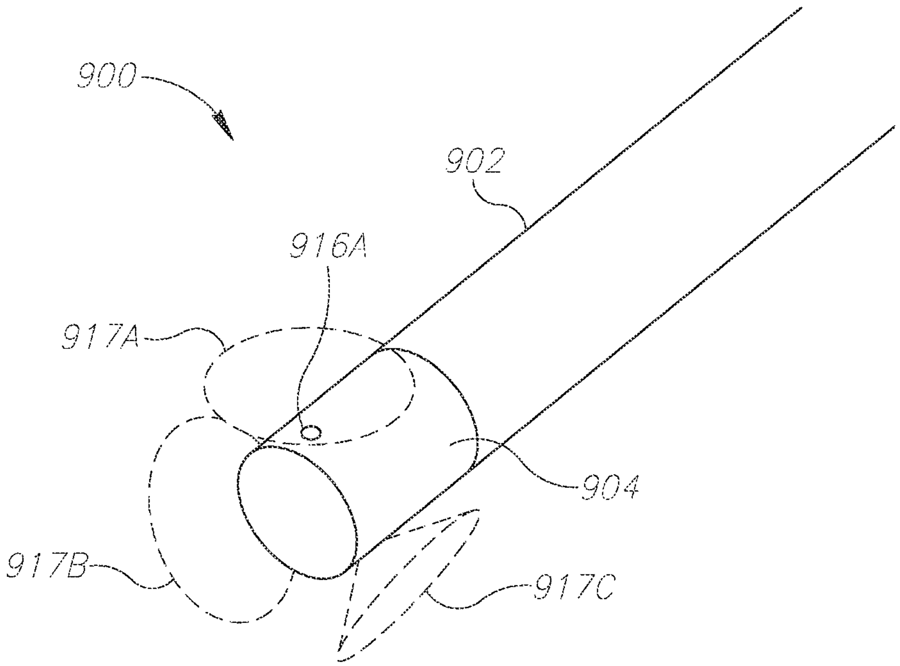
FIG. 9 shows a perspective view of a multi-camera endoscope, according to some embodiments.

Reference is now made to FIG. 9, which shows a perspective view of a multi-camera endoscope, according to some embodiments. Endoscope 900 is similar to endoscope 800 how ever does not include a working channel Elongated shaft 902, tip section 904, side-pointing cameras 916*a*, 916*b* (not shown) and 916*c* (not shown), and their respective fields of view 917*a-c* may be similar to elongated shaft 802, tip section 804, side-pointing cameras 816*a*, 816*b* (not shown) and 816*c* (not shown), and their respective fields of view 817*a-c* of endoscope 800.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A tip section of a multi-camera endoscope, wherein said tip section is defined by a housing having a cylindrical wall and a distal face and wherein the distal face is perpendicular to the cylindrical wall, the tip section comprising:

a front-pointing camera positioned on said distal face, wherein the front-pointing camera has a field of view of at least 120 degrees, a front-pointing image sensor, and a front lens assembly, and a discrete front illuminator associated therewith;

a first side-pointing camera positioned on said cylindrical wall and within an aperture in the cylindrical wall, wherein said first side-pointing camera has a field of view of at least 120 degrees, a first side-pointing image sensor, and a first side lens assembly, pointing in a first side direction, and positioned in proximity to the distal face of said tip section, wherein the aperture is in a depression in the cylindrical wall;

a second side-pointing camera positioned on said cylindrical wall, wherein said second side-pointing camera has a field of view of at least 120 degrees, a second side-pointing image sensor, and a second side lens assembly, pointing in a direction essentially opposite to the first side direction and positioned in proximity to said distal face of said tip section, a fluid injector positioned on said cylindrical wall and within the depression in the cylindrical wall;

wherein each of said side-pointing cameras has a discrete side illuminator associated therewith, wherein the fields of view of the front-pointing camera and first side-pointing camera are at least partially overlapping, such that an object of interest viewed via the first side-pointing camera remains in the field of view of the first side-pointing camera while the tip section is being turned towards the object, and at least until the object becomes visible through the front-pointing camera and wherein the fields of view of the front-pointing camera and second side-pointing camera are at least partially overlapping, such that an object of interest viewed via the second side-pointing camera remains in the field of view of the second side-pointing camera while the tip section is being turned towards the object, and at least until the object becomes visible through the front-pointing camera; and a working channel configured for insertion of a surgical tool, wherein the working channel extends through the tip section and has an exit opening on said distal face.

2. The tip section according to claim 1, wherein the fluid injector is a first fluid injector, and the tip section further comprises a second fluid injector for inflating and/or cleaning a body cavity into which the endoscope is inserted, wherein the second fluid injector has an exit opening on said distal face.

3. The tip section according to claim 1, wherein the fluid injector is a first fluid injector, and the tip section further comprises a second fluid injector configured for cleaning at least one of said front-pointing camera and said discrete front illuminator, wherein the second fluid injector has an exit opening on said distal face.

4. The tip section according to claim 1, further comprising one or more additional fluid injectors configured for cleaning the second side-pointing camera and said discrete side illuminators.

5. The tip section according to claim 1, comprising three or more side-pointing cameras positioned essentially at equal distances from each other along the cylindrical wall of said tip section.

6. The tip section according to claim 1, wherein said discrete front illuminator comprises a light-emitting diode (LED).

7. The tip section according to claim 1, wherein each of said discrete side illuminators comprises a light-emitting diode (LED).

8. The tip section according to claim 1, wherein each of said discrete front and side illuminators comprises a light-emitting diode (LED).

9. The tip section according to claim 1, wherein said endoscope is a colonoscope.

10. A multi-camera endoscope comprising:

an elongated shaft terminating with a tip section turnable by way of a bending section, wherein said tip section comprises:

a housing having a cylindrical wall and a distal face, wherein the distal face is perpendicular to the cylindrical wall;

a front-pointing camera positioned on said distal face, wherein the front-pointing camera has a field of view of at least 120 degrees, a front-pointing image sensor, and a front lens assembly, and a discrete front illuminator associated therewith;

a first side-pointing camera positioned on said cylindrical wall and within an aperture in the cylindrical wall, wherein the first side-pointing camera has a field of view of at least 120 degrees, a first side-pointing image sensor, and a first side lens assembly, pointing in a first side direction, and positioned in proximity to the distal face of said tip section, wherein the aperture is in a depression in the cylindrical wall;

a second side-pointing camera positioned on said cylindrical wall, wherein the second side-pointing camera has a field of view of at least 120 degrees, a second side-pointing image sensor, and a second side lens assembly, pointing in a direction essentially opposite to the first side direction and positioned in proximity to the distal face of said tip section, wherein each of said side-pointing cameras has a discrete side illuminator associated therewith, a fluid injector positioned on said cylindrical wall and within the depression in the cylindrical wall, wherein the fields of view of the front-pointing camera and first side-pointing camera are at least partially overlapping, such that an object of interest viewed via the first side-pointing camera remains in the field of view of the first side-pointing camera while the tip section is being turned towards the object, and at least until the object becomes visible through the front-pointing camera and wherein the fields of view of the front-pointing camera and second side-pointing camera are at least partially overlapping, such that an object of interest viewed via the second side-pointing camera remains in the field of view of the second side-pointing camera while the tip section is being turned towards the object, and at least until the object becomes visible through the front-pointing camera; and a working channel configured for insertion of a surgical tool, wherein the working channel extends through the tip section and has an exit opening on said distal face; and a display configured to display images from each of the front-pointing camera, first side-pointing camera, and second side-pointing camera.

11. The endoscope according to claim 10, wherein the fluid injector is a first fluid injector, and wherein said tip section further comprises a second fluid injector for inflating and/or cleaning a body cavity into which the endoscope is inserted, wherein the second fluid injector extends through the tip section and has an exit opening on said distal face.

12. The endoscope according to claim 10, wherein the fluid injector is a first fluid injector, and wherein said tip section further comprises a second fluid injector configured for cleaning at least one of said front-pointing camera and said discrete front illuminator wherein the second fluid injector extends through the tip section and has an exit opening on said distal face.

13. The endoscope according to claim 10, wherein said tip section further comprises at least one additional side fluid injector configured for cleaning the second side-pointing camera and/or said discrete side illuminators.

14. The endoscope according to claim 10, wherein said tip section comprises three or more side-pointing cameras positioned essentially at equal distances from each other along the perimeter of said tip section.

15. The endoscope according to claim 10, wherein said discrete front illuminator comprises a light-emitting diode (LED).

16. The endoscope according to claim 10, wherein each of said discrete side illuminators comprises a light-emitting diode (LED).

17. The endoscope according to claim 10, wherein each of said discrete front and side illuminators comprises a light-emitting diode (LED).

18. The endoscope according to claim 10, wherein said endoscope is a colonoscope.

* * * * *